US005567372A

United States Patent [19]
Nohr et al.

[11] Patent Number: 5,567,372
[45] Date of Patent: Oct. 22, 1996

[54] METHOD FOR PREPARING A NONWOVEN WEB CONTAINING ANTIMICROBIAL SILOXANE QUATERNARY AMMONIUM SALTS

[75] Inventors: Ronald S. Nohr, Roswell; John G. MacDonald, Decatur, both of Ga.

[73] Assignee: Kimberly-Clark Corporation, Neenah, Wis.

[21] Appl. No.: 249,788

[22] Filed: May 26, 1994

Related U.S. Application Data

[63] Continuation-in-part of Ser. No. 76,529, Jun. 11, 1993, abandoned.

[51] Int. Cl.$^6$ .............................. D04H 3/00; D01D 5/04; D01F 1/10
[52] U.S. Cl. ...................... 264/103; 264/211; 424/404; 424/443; 524/188; 525/102; 556/423
[58] Field of Search ............................ 264/103, 211, 264/211.14; 424/404, 443; 556/423; 524/188; 525/102

[56] References Cited

U.S. PATENT DOCUMENTS

| | | | |
|---|---|---|---|
| 3,016,599 | 1/1962 | Perry, Jr. | 28/78 |
| 3,034,957 | 6/1962 | Smith | 424/443 |
| 3,161,622 | 12/1964 | Harrington, Jr. | 424/404 |
| 3,279,986 | 12/1965 | Hyman | 424/404 |
| 3,341,394 | 9/1967 | Kinney | 161/72 |
| 3,655,862 | 4/1972 | Dorschner et al. | 264/290 |
| 3,692,618 | 9/1972 | Dorschner et al. | 161/72 |
| 3,704,198 | 11/1972 | Prentice | 161/148 |
| 3,705,068 | 12/1972 | Dobo et al. | 156/441 |
| 3,755,527 | 4/1973 | Keller et al. | 364/210 |
| 3,802,817 | 4/1974 | Matsuki et al. | 425/66 |
| 3,849,241 | 11/1974 | Butin et al. | 161/169 |
| 3,853,651 | 12/1974 | Porte | 156/73.6 |
| 3,978,185 | 8/1976 | Buntin et al. | 264/93 |
| 4,006,176 | 2/1977 | Heckert et al. | 260/448.2 |
| 4,064,605 | 12/1977 | Akiyama et al. | 28/103 |
| 4,091,140 | 5/1978 | Harmon | 428/288 |
| 4,100,319 | 7/1978 | Schwartz | 428/171 |
| 4,100,324 | 7/1978 | Anderson et al. | 428/288 |
| 4,118,531 | 10/1978 | Hauser | 428/224 |
| 4,340,563 | 7/1982 | Appel et al. | 264/518 |
| 4,405,297 | 9/1983 | Appel et al. | 425/72 |
| 4,434,204 | 2/1984 | Hartman et al. | 428/198 |
| 4,627,811 | 12/1986 | Greiser et al. | 425/72 |
| 4,644,045 | 2/1987 | Fowells | 526/348 |
| 4,663,220 | 5/1987 | Wisneski et al. | 428/221 |
| 4,895,964 | 1/1990 | Margida | 556/425 |
| 4,923,914 | 5/1990 | Nohr et al. | 524/99 |
| 4,935,232 | 6/1990 | McIntosh | 424/404 |
| 5,069,907 | 12/1991 | Mixon | 424/404 |
| 5,124,466 | 6/1992 | Azechi et al. | 556/425 |
| 5,283,023 | 2/1994 | Nohr | 264/103 |
| 5,300,167 | 4/1994 | Nohr et al. | 156/167 |

FOREIGN PATENT DOCUMENTS 1-197557  8/1989  Japan.

94/29325  12/1994  WIPO.

OTHER PUBLICATIONS

Chemical Abstracts, vol. 121, No. 18, Oct. 31, 1994, Columbus, Ohio, U.S.; Abstract No. 212892j, Nohr, R.S., et al., "New Biomaterials Through Surface Segregation Phenomenon: New Quaternary Ammonium Compounds As Antibacterial Agents" p. 543; see abstract and J. Biomater. Sci., Polym. Ed., vol. 5, No. 6, 1994, pp. 607–619.
Derwent abstract of Japanese Patent Document 4011–078 (Jan. 16, 1992).
Derwent abstract of Japanese Patent Document 4011–079 (Jan. 16, 1992).
Derwent abstract of Japanese Patent Document 4011–080 (Jan. 16, 1992).
Derwent abstract of Japanese Patent Document 02–157285 (Jun. 18, 1990).
Derwent abstract of Korean Patent Document 9103–655 (Jun. 8, 1991).
Block, S. S., "Disinfection, Sterilization, and Preservation," Third Edition, 1983, pp. 48–49.
V. A. Wente, "Superfine Thermoplastic Fibers", vol. 48, No. 8, pp. 1342–1346 (1956).
V. A. Wente, et al., "Manufacture of Superfine Organic Fibers", NRL Report 4364 (111437), dated May 25, 1954.
Robert R. Butin and Dwight T. Lohkamp, "Melt Blowing—A One–Step Web Process for New Nonwoven Products", Journal of the Technical Assoc of the Pulp & Paper Industry, vol. 56, No. 4, pp. 74–77 (1973).
Introduction to Organic Chemistry, 2nd Ed, pp. 763–766.
E. Nester, Microbiology, 2nd Ed, 1978 p. 110.
Volk, Wesley A., Essentials of medical Microbiology, pp. 46–51.
R. A. Robinson, et al., Appl. Environ. Microbiol., 54, 158 (1988).

Primary Examiner—D. R. Wilson
Attorney, Agent, or Firm—William E. Maycock

[57] ABSTRACT

A method for preparing a nonwoven web having antimicrobial properties which involves melting a melt-extrudable thermoplastic composition, extruding the molten composition through multiple orifices to form streams of molten composition, cooling the streams of molten composition to form fibers, and randomly depositing the fibers on a moving foraminous surface to form a web. The thermoplastic composition includes a thermoplastic material and an additive. The additive is an antimicrobial siloxane quaternary ammonium salt which can be either of two general classes: (1) a trisiloxane having a pendent quaternary ammonium group and a molecular weight of from about 600 to about 1,700; and (2) an ABA-type siloxane having a polydispersity of up to about 3.0 and a weight-average molecular weight of from about 800 to about 2,000, in which a central siloxane moiety is terminated at each end by a quaternary ammonium salt group. The anion in general can be any anion which does not adversely affect the thermal stability of the salt.

9 Claims, 17 Drawing Sheets

I

V

VII

VIII

METHOD FOR PREPARING A NONWOVEN WEB CONTAINING ANTIMICROBIAL SILOXANE QUATERNARY AMMONIUM SALTS

This is a continuation-in-part of application Ser. No. 08/076,529, filed on Jun. 11, 1993 now abandoned in the names of Ronald Sinclair Nohr and John Gavin MacDonald.

CROSS-REFERENCE TO RELATED APPLICATION

Polysiloxane quaternary ammonium salts are employed in a method of preparing a nonwoven web having delayed wettability, which method is described and claimed in commonly assigned U.S. Pat. No. 5,300,167, filed on Jun. 11, 1993 in the names of Ronald Sinclair Nohr and John Gavin MacDonald.

BACKGROUND OF THE INVENTION

The present invention relates to siloxane quaternary ammonium salts.

Traditional melt-extrusion processes for the formation of a nonwoven web from a thermoplastic polymer typically involve melting the thermoplastic polymer, extruding the molten polymer through multiple orifices to form a plurality of threadlines or filaments, attenuating the filaments by entrainment in a rapidly moving first stream of gas, cooling the filaments with a second stream of gas, and randomly depositing the attenuated filaments, or fibers, on a moving foraminous surface. The most common and well known of these processes are meltblowing, coforming, and spunbonding. The nonwoven webs obtained by these processes are widely used in a variety of products, but especially in such disposable absorbent products as diapers; incontinent products; feminine care products, such as tampons and sanitary napkins; wipes; sterilization wraps; surgical drapes and related materials; hospital gowns and shoe covers; and the like, to name but a few.

There is an increasing interest in the utilization of nonwoven webs which have antimicrobial properties. The traditional means for providing such webs has been to simply topically treat the already-formed nonwoven web with a solution of an antimicrobial agent. This involves additional processing steps and typically requires drying the treated web to remove water or other solvent in which the antimicrobial agent is dissolved. Because the antimicrobial agent typically is water soluble, it is easily removed from the web by water. This obviously is a serious disadvantage for nonwoven webs which will be repeatedly used or placed in contact with water.

It is, of course, known to melt-extrude a mixture of an additive and a thermoplastic polymer to prepare fibers. In some instances, the additive must be forced, or "bloomed", to the surfaces of the fibers by subjecting them to a post-heat treatment step. The additive to be bloomed usually is a nonionic surfactant, such as an alkylphenoxy polyether.

In other instances, a surface-segregatable, melt-extrudable thermoplastic composition is employed which includes at least one thermoplastic polymer and at least one additive which typically is a polysiloxane polyether. Such surface segregation now appears to be best explained on the basis of micelle formation. Briefly, a relatively low molecular weight additive is miscible with the polymer at melt extrusion temperatures, forming an unstable emulsion characterized by metastable micellar structures. Upon extrusion, during which a rapid increase in shear rate is experienced, the additive is believed to break free from the metastable micelle "aggregate" and molecularly diffuse to the fiber surfaces. Such diffusion is driven in part by both a loss of additive compatibility and a potential drop in interfacial free energy.

However, the goal of providing a compound to be included as an additive in a thermoplastic composition for the preparation of antimicrobial nonwoven webs presents at least three challenges. First, the additive should undergo surface segregation upon melt-extruding the additive-containing thermoplastic composition to form fibers. As already noted, the compounds of the present invention do, in fact, migrate to the fiber surfaces. The alternative is to use an amount of the additive which is sufficiently large so as to assure that at least some additive is present at the surfaces of the fibers, but this significantly increases fiber spinning problems and increases the possibility of additive degradation. In addition, both material and manufacturing costs are increased. Second, assuming the additive is present at the surfaces of the fibers, it must be capable of imparting antimicrobial properties thereto. Third, the additive must be relatively stable during the melt-extrusion process.

SUMMARY OF THE INVENTION

In response to the discussed difficulties and problems encountered in the prior art, two classes of novel siloxane quaternary ammonium salts now have been discovered which meet all three of the above requirements and, as will be demonstrated later, do so to an unexpected degree. That is, such salts undergo surface segregation upon melt-extrusion of the thermoplastic composition of which they are a part, they impart antimicrobial properties to the surfaces of the fibers, and they are relatively stable during the melt-extrusion process. In addition, they form an extended antimicrobial surface, i.e., an antimicrobial surface which extends below the air/fiber interfacial surface, which affords the potential for durable antimicrobial properties.

In light of the unexpected results described herein, it appears that the compounds of the present invention enhance the loss of additive compatibility just described. This increases the rate of diffusion which forces more additive molecules to the surface before fiber solidification stops the migration. Consequently, unexpectedly high levels of additive were observed to have migrated to the surfaces of the fibers.

Accordingly, the present invention provides a siloxane quaternary ammonium salt having either the general formula A,

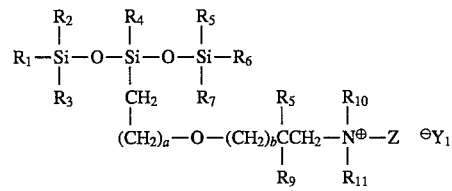

wherein:

(1) each of $R_1$–$R_7$ is independently selected from the group consisting of monovalent $C_1$–$C_{20}$ alkyl, phenyl, and phenyl-substituted $C_1$–$C_{20}$ alkyl groups, in which each phenyl can be substituted or unsubstituted;

(2) each of $R_8$ and $R_9$ is a monovalent group independently selected from the group consisting of (a) hydrogen and (b) monovalent alkyl, cycloalkyl, aryl, and heterocyclic groups and combinations thereof having up to about 30 carbon atoms, except that both $R_8$ and $R_9$ cannot be hydrogen; or, when taken together in combination with the carbon atom to which they are attached, $R_8$ and $R_9$ represent a carbonyl group;

(3) each of $R_{10}$ and $R_{11}$ is an independently selected monovalent $C_1$–$C_{20}$ alkyl group;

(4) a represents an integer from 1 to about 20;

(5) b represents an integer from 1 to about 20;

(6) Z is a monovalent group having from about 8 to about 30 carbon atoms and selected from the group consisting of alkyl, cycloalkyl, aryl, and heterocyclic groups, and combinations thereof, wherein Z is terminated by an alkyl moiety which includes at least about 8 carbon atoms in a single continuous chain;

(7) $Y_1$ is an anion; and (8) the siloxane quaternary ammonium salt has a molecular weight of from about 600 to about 1,700;

or the general formula B,

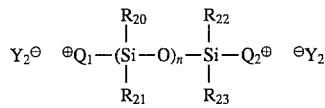

wherein:

(1) each of $R_{20}$–$R_{23}$ is independently selected from the group consisting of monovalent $C_1$–$C_{20}$ alkyl, phenyl, and phenyl-substituted $C_1$–$C_{20}$ alkyl groups, in which each phenyl can be substituted or unsubstituted;

(2) n represents an integer of from 1 to about 19;

(3) each of $Q_1$ and $Q_2$ represents an independently selected quaternary ammonium group having the general formula,

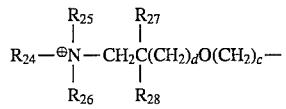

in which:

(a) $R_{24}$ is a monovalent alkyl group having from about 8 to about 30 carbon atoms, at least about 8 carbon atoms of which make up a single continuous chain;

(b) $R_{25}$ and $R_{26}$ are independently selected monovalent $C_1$–$C_{20}$ alkyl groups;

(c) each of $R_{27}$ and $R_{28}$ is a monovalent group independently selected from the group consisting of (i) hydrogen and (ii) monovalent alkyl, cycloalkyl, aryl, and heterocyclic groups and combinations thereof having up to about 30 carbon atoms, except that both $R_{27}$ and $R_{28}$ cannot be hydrogen; or, when taken together in combination with the carbon atom to which they are attached, $R_{27}$ and $R_{28}$ represent a carbonyl group;

(d) c represents an integer of from 2 to about 20; and (e) d represents an integer of from 2 to about 20;

(4) $Y_2$ represents an anion; and (5) the siloxane quaternary ammonium salt has a polydispersity of up to about 3.0 and a weight-average molecular weight of from about 800 to about 2,000.

The present invention also contemplates a melt-extrudable composition which includes at least one melt-extrudable material adapted to be shaped into a product by melt extrusion and at least one additive which includes a siloxane-containing moiety and an antimicrobial moiety. Melt-extruded products contemplated by the present invention include a fiber and a nonwoven web which includes a plurality of fibers.

The additive is adapted to surface segregate upon extrusion of the composition to impart antimicrobial properties to a surface of the product. The antimicrobial moiety may be a quaternary ammonium salt moiety. In general, the additive will be present in the composition at a level which is sufficient to impart antimicrobial properties to the product. The composition may be a melt-extrudable thermoplastic composition. In one embodiment, the melt-extrudable thermoplastic composition is a polyolefin. For example, the composition may include at least one thermoplastic polyolefin and at least one additive having either the general formula A or the general formula B, above.

The present invention further contemplates that the quaternary ammonium salt moiety of the additive may be part of a siloxane quaternary ammonium salt. Desirably, the siloxane quaternary ammonium salt will have either general formula A or general formula B. The thermal stability of a salt represented by general formula A or B is enhanced by the presence of no more than one hydrogen atom on each β-carbon atom of the quaternary ammonium salt moiety thereof. Desirably, each β-carbon atom will not have any hydrogen atoms attached to it.

DETAILED DESCRIPTION OF THE INVENTION

Figure 1:
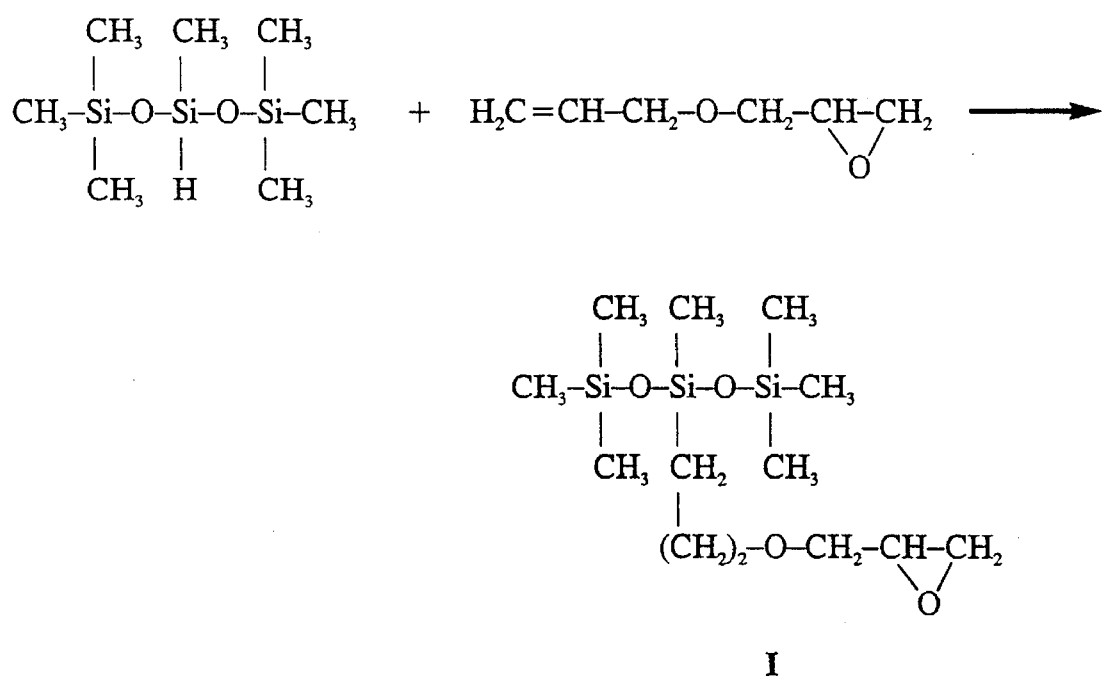
FIGS. 1–10 illustrate the various chemical reactions involved in preparing compounds of the present invention as described in Examples 1–10.

As used herein, the term "stable" is used with reference to an antimicrobial compound of the present invention to mean that the compound is sufficiently thermally stable during melt processing to form fibers in which the compound has segregated to the surfaces of the fibers in an amount which is sufficient to impart antimicrobial activity thereto. Thus, some thermal degradation is acceptable, provided at least about 65 percent of the compound present in the thermoplastic composition to be melt extruded survives the melt extrusion process.

For convenience, the phrase "internal additive," as well as variations thereof, is used herein with reference to the compounds of the present invention. The phrase implies, as taught herein, the inclusion of a compound of the present invention in a melt-extrudable material, e.g., a thermoplastic polymer, to give a melt-extrudable or thermoplastic composition which subsequently is melt-processed to form a nonwoven web or other shaped article.

As used herein, the terms "shaped article" and "product" are synonyms and are meant to include any article or product which is formed by a melt-extrusion process, regardless of the size or shape of the article. As a practical matter, the present disclosure is directed primarily to melt-extruded fibers and nonwoven webs comprised of such fibers. Nevertheless, other shaped articles or products are deemed to come within the spirit and scope of the present invention.

The term "extended antimicrobial surface" is used herein to refer to the region of a fiber (or other shaped article) prepared in accordance with the present invention which extends from the interfacial surface, e.g., the air/fiber (or nonfiber/fiber) interface, to a depth of roughly 100Å (or perhaps even further), which region consists essentially of antimicrobial compound.

The term "melt-extrudable material" is meant to include any material adapted to be shaped into a product by melt extrusion. Thus, the term includes both thermosetting and thermoplastic materials. Particularly useful thermoplastic materials are the thermoplastic polyolefins.

In general, the term "thermoplastic polyolefin" is used herein to mean any thermoplastic polyolefin which can be used for the preparation of shaped articles by melt extrusion, e.g., fibers and nonwoven webs. Examples of thermoplastic polyolefins include polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, poly(vinyl acetate), poly(vinylidene chloride), polystyrene, and the like. In addition, such term is meant to include blends of two or more polyolefins and random and block copolymers prepared from two or more different unsaturated monomers.

Particularly useful polyolefins are those which contain only hydrogen and carbon atoms and which are prepared by the addition polymerization of one or more unsaturated monomers. Examples of such polyolefins include, among others, polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polystyrene, and the like. Because of their commercial importance, the most significant polyolefins are polyethylene and polypropylene.

The term "monovalent $C_1$-$C_{20}$ alkyl" is used herein to encompass such monovalent groups as methyl, ethyl, propyl, isopropyl, butyl, 2-butyl, isobutyl, t-butyl, pentyl, isopentyl, 2-pentyl, 3-pentyl, 2-methyl-2-butyl, hexyl, 2-hexyl, 3-hexyl, 4-methyl-2-pentyl, 3,3-dimethylbutyl, heptyl, 2-heptyl, 3-heptyl, 4-heptyl, 3-methyl-2-hexyl, 2,3-dimethylpentyl, octyl, 2-octyl, 3-octyl, 4-octyl, 3-ethylhexyl, 3-methylheptyl, nonyl, 3-nonyl, 5-nonyl, 4-methyloctyl, isodecyl, 2,5,5-trimethylheptyl, undecyl, dodecyl, 3-tridecyl, tetradecyl, 2-tetradecyl, 3,4,6-trimethylundecyl, 4-pentadecyl, hexadecyl, isoheptadecyl, octadecyl, 2-octadecyl, nonadecyl, eicosyl, and the like. The phrase "monovalent phenyl and phenyl-substituted $C_1$-$C_{20}$ alkyl groups, in which each phenyl can be substituted or unsubstituted" includes by way of illustration only, phenyl, o-tolyl, m-tolyl, p-tolyl, 3,4-dimethylphenyl, 3,5-dimethylphenyl, 3-methyl-4-ethylphenyl, benzyl, 2,4-diethylbenzyl, 2-phenylpropyl, 2-(3-methoxyphenyl)-butyl, phenylpentyl, 3-(4-methoxyphenyl)hexyl, 4-phenyloctyl, 3-benzylundecyl, 5-phenyl-2-dodecyl, 3-(o-tolyl)tetradecyl, 3-phenoxyheptadecyl, 2,4-dimethyl-6-phenylhexadecyl, phenyleicosyl, and the like.

As used herein, the phrase "having up to about 30 carbon atoms", when used in conjunction with the phrase "monovalent alkyl, cycloalkyl, aryl, and heterocyclic groups and combinations thereof", means that each type of group and combinations thereof can contain up to about 30 carbon atoms. Thus, the approximately 30 carbon atoms is a limit on the total number of carbon atoms in the group, regardless of the natures or numbers of groups of which the "monovalent group" is composed. The lower limit is the minimum number of carbon atoms permitted by the type of group, as is well known by those having ordinary skill in the art. By way of illustration, a cycloalkyl group must have at least three carbon atoms in the ring. As a practical matter, however, cycloalkyl groups having from 3 to 5 carbon atoms are more strained than rings having 6 or more carbon atoms and, as a consequence, may be less stable. The use of larger ring structures, i.e., cycloalkyl groups having at least 6 carbon atoms, will reduce such strain-related instability.

Examples of the various monovalent alkyl, cycloalkyl, aryl, and heterocyclic groups and combinations thereof include, by way of illustration only, the monovalent $C_1$-$C_{20}$ alkyl groups exemplified above and such groups as heneicosyl, 6-(1-methylpropyl)-2-heptadecyl, 3-docosyl, 5-ethylheneicosyl, hexacosyl, 3-methylpentacosyl, heptacosyl, 3,7,8-trimethyltetracosyl, octacosyl, 5-octacosyl, 2-nonacosyl, 4-propylhexacosyl, 3-triacontyl, 6-ethyl-2-octacosyl, cyclopropyl, methylcyclopropyl, cyclobutyl, cyclopentyl, cyclohexyl, cycloheptyl, 3-methylcyclohexyl, 2-ethylcyclopentyl, 2-bicyclo[2.2.1]heptyl, cyclooctyl, 4-ethylcyclohexyl, 8-bicyclo[3.2.1]octyl, cyclononyl, cyclodecyl, 2,3,5-trimethylcycloheptyl, 2-bicyclo[4.4.0]decyl, cyclopentadecyl, cycloheneicosyl, cyclohexacosyl, cyclotriacontyl, phenyl, o-tolyl, m-tolyl, p-tolyl, 3,4-dimethylphenyl, 3,5-dimethylphenyl, 3-methyl-4-ethylphenyl, benzyl, 2,4-diethylbenzyl, 4-hexadecylbenzyl, 3-methyl-5-phenylhexyl, 4-cyclohexylphenyl, 1-naphthyl, 2-naphthyl, 1-anthracyl, 9,10-dihydro-2-anthracyl, 1-phenanthryl, 2-phenanthryl, 3-phenanthryl, 4-phenanthryl, 9-phenanthryl, 2-pentacenyl, 1-cornenyl, phenyl, 1-naphthyl, 2-naphthyl, o-tolyl, m-tolyl, p-tolyl, 3,4-dimethylphenyl, 3,5-dimethylphenyl, 3-methyl-4-ethylphenyl, pyrrolidinyl, piperidino, 2-piperidinoethyl, 3-piperidyl, 2-(trimethylsilyl)ethyl, 1-biphenylyl, benzyl, 2,4-diethylbenzyl, 4-hexadecylbenzyl, 3-methyl-5-phenylhexyl, 4-cyclohexylphenyl, 2-(trimethylsilyl)ethyl, 1-biphenylyl, cyclohexylmethyl, 4-cyclopentylhexyl, and the like.

Based on the foregoing, examples of various subgroups, such as monovalent $C_6$-$C_{28}$ alkyl groups, monovalent $C_8$-$C_{23}$ alkyl groups, and the like will be readily determined by those having ordinary skill in the art. In addition, groups such as those listed above may not be suitable in every instance. Stated differently, a particular group listed above may not meet all of the requirements for a given substituent. In such case, it is only necessary to add to the particular group whatever is necessary for it to meet the requirements for the given substituent. For example, as is explained in detail hereinafter, some groups should have a terminal alkyl moiety which includes at least about 8 carbon atoms in a single continuous chain. A benzyl group does not have the required terminal alkyl moiety. However, such requirement is met by, e.g., a 4-octylbenzyl group or a 4-hexadecylbenzyl group. Nevertheless, one having ordinary skill in the art can readily determine, based on the present disclosure, which groups are suitable for any given substituent of an antimicrobial siloxane quaternary ammonium salt of the present invention without the need for undue experimentation.

The siloxane quaternary ammonium salt of the present invention has either the general formula A,

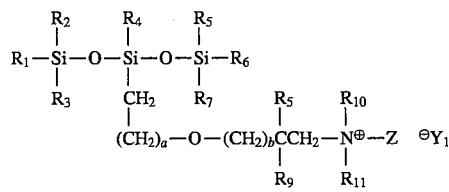

wherein:

(1) each of $R_1$–$R_7$ is independently selected from the group consisting of monovalent $C_1$-$C_{20}$ alkyl, phenyl, and phenyl-substituted $C_1$-$C_{20}$ alkyl groups, in which each phenyl can be substituted or unsubstituted;

(2) each of $R_8$ and $R_9$ is a monovalent group independently selected from the group consisting of (a) hydrogen and (b) monovalent alkyl, cycloalkyl, aryl, and heterocyclic groups and combinations thereof having up to about 30 carbon atoms, except that both $R_8$ and $R_9$ cannot be hydrogen; or, when taken together in combination with the carbon atom to which they are attached, $R_8$ and $R_9$ represent a carbonyl group;

(3) each of $R_{10}$ and $R_{11}$ is an independently selected monovalent $C_1$–$C_{20}$ alkyl group;

(4) a represents an integer from 1 to about 20;

(5) b represents an integer from 1 to about 20;

(6) Z is a monovalent group having from about 8 to about 30 carbon atoms and selected from the group consisting of alkyl, cycloalkyl, aryl, and heterocyclic groups, and combinations thereof, wherein Z is terminated by an alkyl moiety which includes at least about 8 carbon atoms in a single continuous chain;

(7) Y is an anion; and (8) said siloxane quaternary ammonium salt has a molecular weight of from about 600 to about 1,700;

or the general formula B,

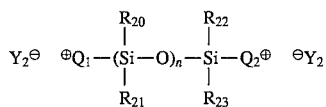

wherein:

(1) each of $R_{20}$–$R_{23}$ is independently selected from the group consisting of monovalent $C_1$–$C_{20}$ alkyl, phenyl, and phenyl-substituted $C_1$–$C_{20}$ alkyl groups, in which each phenyl can be substituted or unsubstituted;

(2) n represents an integer of from 1 to about 19;

(3) each of $Q_1$ and $Q_2$ represents an independently selected quaternary ammonium group having the general formula,

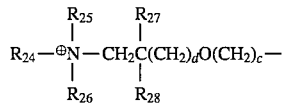

in which:

(a) $R_{24}$ is a monovalent alkyl group having from about 8 to about 30 carbon atoms, at least about 8 carbon atoms of which make up a single continuous chain;

(b) $R_{25}$ and $R_{26}$ are independently selected monovalent $C_1$–$C_{20}$ alkyl groups;

(c) each of $R_{27}$ and $R_{28}$ is a monovalent group independently selected from the group consisting of (i) hydrogen and (ii) monovalent alkyl, cycloalkyl, aryl, and heterocyclic groups and combinations thereof having up to about 30 carbon atoms, except that both $R_{27}$ and $R_{28}$ cannot be hydrogen; or, when taken together in combination with the carbon atom to which they are attached, $R_{27}$ and $R_{28}$ represent a carbonyl group;

(d) c represents an integer of from 2 to about 20; and (e) d represents an integer of from 2 to about 20.

(4) $Y_2$ represents an anion; and (5) said siloxane quaternary ammonium salt has a polydispersity of up to about 3.0 and a weight-average molecular weight of from about 800 to about 2,000.

As stated above, each of $R_1$–$R_7$ is independently selected from the group consisting of monovalent $C_1$–$C_{20}$ alkyl, phenyl, and phenyl-substituted $C_1$–$C_{20}$ alkyl groups, in which each phenyl can be substituted or unsubstituted. In addition, each of $R_{10}$ and $R_{11}$ is an independently selected monovalent $C_1$–$C_{20}$ alkyl group. For example, each of $R_1$–$R_7$, $R_{10}$, and $R_{11}$ can be independently selected from the group consisting of monovalent $C_1$–$C_4$ alkyl, phenyl, and phenyl-substituted $C_1$–$C_4$ alkyl groups, in which each phenyl can be substituted or unsubstituted. As a further example, each of $R_1$–$R_7$, $R_{10}$, and $R_{11}$ independently can be a methyl group or an ethyl group. Desirably, each of $R_1$–$R_7$, $R_{10}$, and $R_{11}$ will be a methyl group.

As already noted, each of $R_8$ and $R_9$ independently is selected from the group consisting of (a) hydrogen and (b) monovalent alkyl, cycloalkyl, aryl, and heterocyclic groups and combinations thereof having up to about 30 carbon atoms, except that both $R_8$ and $R_9$ cannot be hydrogen. Alternatively, when taken together in combination with the carbon atom to which they are attached, $R_8$ and $R_9$ represent a carbonyl group.

By way of example, each of $R_8$ and $R_9$ is an independently selected monovalent $C_1$–$C_4$ alkyl group or, when taken together in combination with the carbon atom to which they are attached, $R_8$ and $R_9$ represent a carbonyl group. As a further example, each of $R_8$ and $R_9$ independently can be a methyl group or an ethyl group, or, when taken together in combination with the carbon atom to which they are attached, $R_8$ and $R_9$ represent a carbonyl group. Desirably, each of $R_8$ and $R_9$ will be a methyl group or, when taken together in combination with the carbon atom to which they are attached, $R_8$ and $R_9$ represent a carbonyl group.

In general, each of a and b independently represent an integer from 1 to about 20. For example, each of a and b independently represent an integer from 1 to about 5. Desirably, a is 2 or 3 and b is 1 or 2.

Z is a monovalent group having from about 8 to about 30 carbon atoms. It is selected from the group consisting of alkyl, cycloalkyl, aryl, and heterocyclic groups, and combinations thereof. In addition, Z is terminated by an alkyl moiety which includes at least about 8 carbon atoms in a single continuous chain. For example, Z can be an alkyl or alkylphenylalkyl group.

The phrase, "terminated by an alkyl moiety which includes at least about 8 carbon atoms in a single continuous chain," means that, regardless of the nature of Z, it will be terminated by an alkyl moiety which includes at least about 8 carbon atoms in a single continuous chain. Thus, this terminal alkyl moiety will be at the end of Z which is not covalently bonded to the quaternary ammonium nitrogen atom. The carbon atoms making up the single continuous chain can be substituted or unsubstituted, i.e., they can be any one or more of more of such groups as —$CH_2$—, —CHR—, and —CRR'—, with the last group being, for example, one of such groups as —$CH_3$, —$CH_2$R, —CHRR', and —CRR'R", in which each of R, R', and R" represent a substituent other than hydrogen. The term "single continuous chain" means only that the components of the chain are covalently bonded in series, as in the octyl group,

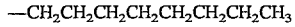

in contrast with, for example, the 2-ethylhexyl or 2,3,4-trimethylpentyl groups,

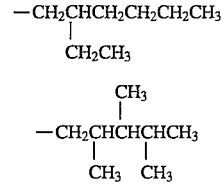

each of which also consists of 8 carbon atoms; the carbon atoms in these latter two groups, however, are not present as a single continuous chain. In certain embodiments, the terminal alkyl moiety will not be branched. In other embodiments, the terminal alkyl moiety will have more than 8 carbon atoms in a single continuous chain.

In some embodiments, Z is a monovalent group having the general formula,

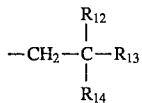

in which each of $R_{12}$–$R_{14}$ is an independently selected monovalent alkyl group wherein the total number of carbon atoms in all of $R_{12}$–$R_{14}$ is from about 6 to about 28 and at least one of $R_{12}$–$R_{14}$ contains at least about 6 carbon atoms in a single continuous chain.

In other embodiments, Z is a monovalent group having the general formula,

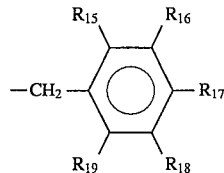

in which each of $R_{15}$–$R_{19}$ is a monovalent group independently selected from the group consisting of hydrogen and alkyl, and wherein the total number of carbon atoms in all of $R_{15}$–$R_{19}$ is from about 8 to about 23, with at least one of $R_{15}$–$R_{19}$ having at least about 6 carbon atoms in a single continuous chain. In some embodiments, each of $R_{15}$, $R_{16}$, $R_{18}$, and $R_{19}$ is hydrogen and $R_{17}$ is hexadecyl.

In general, any anion can be employed in the siloxane quaternary ammonium salt of the present invention which does not contribute significantly to the thermal instability of the salt. By way of illustration only, examples of suitable anions include, among others, halo, such as iodo, bromo, chloro, and fluoro; sulfate; nitrate; phosphate; borate; acetate; p-toluenesulfonate (tosylate); trifluoromethanesulfonate (triflate); nonafluorobutanesulfonate (nonaflate); 2,2,2-trifluoroethanesulfonate (tresylate); fluorosulfonate; and the like. In certain embodiments, the anion is an anion which is a weak base, such as p-toluenesulfonate (tosylate); trifluoromethanesulfonate (triflate); nonafluorobutanesulfonate(nonaflate); 2,2,2-trifluoroethanesulfonate (tresylate); fluorosulfonate; and the like. As used herein, the term "weak base" means a base having an ionization constant of less than one.

The siloxane quaternary ammonium salt having the general formula A typically will have a molecular weight of from about 600 to about 1,700. In some embodiments, the salt will have a molecular weight of from about 800 to about 1,400.

Turning now to the siloxane quaternary ammonium salt having the general formula B, each of $R_{20}$–$R_{23}$ is independently selected from the group consisting of monovalent $C_1$–$C_{20}$ alkyl, phenyl, and phenyl-substituted $C_1$–$C_{20}$ alkyl groups, in which each phenyl can be substituted or unsubstituted. For example, each of $R_{20}$–$R_{23}$ is independently selected from the group consisting of monovalent $C_1$–$C_4$ alkyl, phenyl, and phenyl-substituted $C_1$–$C_4$ alkyl groups, in which each phenyl can be substituted or unsubstituted. As a further example, each of $R_{20}$–$R_{23}$ independently can be a methyl group or an ethyl group. Desirably, each of $R_{20}$–$R_{23}$ will be a methyl group. As yet another example, n represents an integer of from about 5 to about 12.

With respect to $Q_1$ and $Q_2$, $R_{24}$ is a monovalent $C_6$–$C_{30}$ alkyl group, at least about 8 carbon atoms of which make up a single continuous chain, and $R_{25}$ and $R_{26}$ are independently selected monovalent $C_1$–$C_{20}$ alkyl groups. By way of example, $R_{25}$ and $R_{26}$ are independently selected $C_1$–$C_4$ alkyl groups. As another example, each of $R_{25}$ and $R_{26}$ independently is a methyl group or an ethyl group. As yet another example, each of $R_{25}$ and $R_{26}$ is a methyl group.

Each of $R_{27}$ and $R_{28}$ is independently selected from the group consisting of (i) hydrogen and (ii) monovalent alkyl, cycloalkyl, aryl, and heterocyclic groups and combinations thereof having up to about 30 carbon atoms. Alternatively, when taken together in combination with the carbon atom to which they are attached, $R_{27}$ and $R_{28}$ represent a carbonyl group.

Generally, each of c and d independently represent an integer of from 2 to about 20. Desirably, c is 3 or 4 and d is 2 or 3. The anion, $Y_2$, is as defined for the anion, $Y_1$, of the siloxane quaternary ammonium salt having general formula A.

Finally, the siloxane quaternary ammonium salt having the general formula B typically will have a polydispersity of up to about 3.0 and a weight-average molecular weight of from about 800 to about 2,000. In some embodiments, the salt will have a weight-average molecular weight of from about 900 to about 1,400.

In general, the siloxane quaternary ammonium salts of the present invention are prepared by methods which are well known to those having ordinary skill in the art. For example, salts having the general formula A are prepared from a glycidyloxypropyltrisiloxane as described in Examples 1–10, inclusive.

The melt-extrudable composition of the present invention includes at least one melt-extrudable material adapted to be shaped into a product by melt extrusion and at least one additive which includes a siloxane-containing moiety and an antimicrobial moiety. The additive is adapted to surface segregate upon extrusion of the composition to impart antimicrobial properties to a surface of the product. The siloxane-containing moiety of the additive is largely responsible for the ability of the additive to surface segregate. The additive also includes an antimicrobial moiety, from which the additive derives its antimicrobial properties.

As noted earlier, in some embodiments the composition is a melt-extrudable thermoplastic composition. In certain embodiments of a melt-extrudable thermoplastic composition, the melt-extrudable material is a polyolefin. In still other embodiments, the antimicrobial moiety is a quaternary ammonium salt moiety. In still further embodiments, the additive is present in the composition at a level which is sufficient to impart anti-microbial properties to the product.

The present invention contemplates a composition which includes at least one thermoplastic polyolefin and at least one additive having either the general formula A or the general formula B, above. The additive can be monomeric or polymeric. The additive also can be either a liquid or a solid at ambient temperature, although a liquid is easier to work with. In general, the additive will have a molecular weight, or weight-average molecular weight if polymeric, of from about 600 to about 3,000. In some embodiments, the additive will have a molecular weight or weight-average molecular weight of from about 600 to about 2,000. In other embodiments, the additive will have either the general formula A or the general formula B, as defined hereinbefore.

Generally, the additive will be present in the thermoplastic composition at a level which is sufficient to impart antimicrobial properties to the surface of a shaped article formed by melt-extrusion of the composition. The additive typically will be present in the composition at a level of from about 0.1 to about 3 percent by weight, based on the weight of thermoplastic polyolefin. For example, the additive can be present in the composition at a level of from about 0.1 to about 1.5 percent by weight.

The thermoplastic composition of the present invention can be prepared by any number of methods known to those having ordinary skill in the art. For example, the polymer in chip or pellet form and the additive can be mixed mechanically to coat the polymer particles with additive. The additive can be dissolved in a suitable solvent to aid the coating process, although the use of a solvent is not desired. The coated polymer then can be added to the feed hopper of the extruder from which the fibers or other shaped article will emerge. Alternatively, the coated polymer can be charged to a heated compounder, such as a heated twin-screw compounder, in order to disperse the additive throughout the bulk of the polymer. The resulting thermoplastic composition typically is extruded as rods which are fed to a chipper. The resulting chips then serve as the feed stock for a melt-processing extruder. In another method, the additive can be metered into the throat of the hopper which contains the polymer in particulate form and which feeds the extruder. In yet another method, the additive can be metered directly into the barrel of the extruder where it is blended with the molten polymer as the resulting mixture moves toward the die.

Fibers having antimicrobial properties are readily prepared by melt-extruding a melt-extrudable thermoplastic composition of the present invention through multiple orifices to form streams of molten composition which are cooled to form fibers. The melt-extrudable thermoplastic composition includes at least one thermoplastic material and at least one additive which includes a siloxane-containing moiety and an antimicrobial moiety, which additive is adapted to surface segregate upon extrusion of the molten composition to impart antimicrobial properties to the surfaces of the fibers. For example, the molten composition is extruded at a shear rate of from about 50 to about 30,000 sec$^{-1}$ and a throughput of no more than about 5.4 kg/cm/hour.

The method of the present invention for preparing a nonwoven web having antimicrobial properties involves melting a melt-extrudable thermoplastic composition, extruding the molten composition through multiple orifices to form streams of molten composition which are cooled to form fibers which then are randomly deposited on a moving foraminous surface to form a web, wherein the melt-extrudable thermoplastic composition includes at least one thermoplastic material and at least one additive which includes a siloxane-containing moiety and an antimicrobial moiety, which additive is adapted to surface segregate upon extrusion of the molten composition to impart antimicrobial properties to the surfaces of the fibers. For example, the molten composition is extruded at a shear rate of from about 50 to about 30,000 sec$^{-1}$ and a throughput of no more than about 5.4 kg/cm/hour.

The present invention also provides several types of intermediates which are useful for the preparation of the siloxane quaternary ammonium salts described and claimed herein. Procedures for preparing such intermediates are well known to those having ordinary skill in the art, some of which are illustrated by certain of the examples. Such intermediates are represented by general formulas C and D which follow:

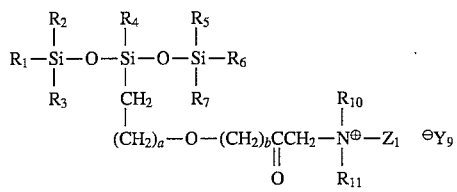

General Formula C wherein $R_1$–$R_7$, $R_{10}$, $R_{11}$, a and b are as already defined, $Z_1$, is a monovalent phenylalkyl group, such as benzyl and the like, and $Y_9$ is an anion as already defined. This type of compound can have a molecular weight of from about 470 to about 1,550.

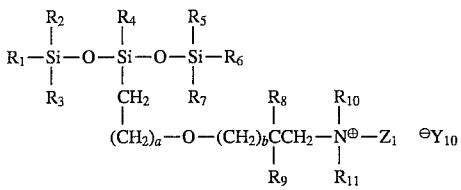

General Formula D wherein $R_1$–$R_{11}$, a, b, and $Z_1$ are as already defined and $Y_{10}$ is an anion as already defined. The compound can have a molecular weight of from about 450 to about 1,500.

The present invention is further described by the examples which follow. Such examples, however, are not to be construed as limiting in any way either the spirit or scope of the present invention. Elemental analyses were preformed by SchwarzkopfMicroanalytical Laboratories (Woodside, N.Y.); samples for elemental analysis were Kogelruhr distilled. $^1$H and $^{13}$C NMR spectra were run on 270 MHz and 360 MHz instruments by Spectral Data Services (Champaign, Ill.); proton spectrum lines are given in values of δ. ESCA analyses were performed by Surface Science Corporation (Mountain View, Calif.).

A siloxane quaternary ammonium salt having general formula A is readily prepared by a synthetic procedure which begins with a glycidyloxypropylheptamethyltrisiloxane and which is described in the examples which follow. For convenience, each step of the reaction sequence comprises a separate example and is illustrated by a separate figure.

EXAMPLE 1

Synthesis of 3-[3-(2,3-Epoxypropoxy)propyl]-1,1,1,3,5,5,5-heptamethyltrisiloxane (I) (FIG. 1)

Although the starting material, 3-[3-(2,3-epoxypropoxy)propyl]-1,1,1,3,5,5,5-heptamethyltrisiloxane (Compound I), can be obtained commercially, it was prepared by the procedure which follows. A 500-ml, three-necked, round-bottomed flask was equipped with a stirrer, addition funnel, and condenser and was flushed continuously with argon. The flask was charged with 22.5 g (0.22 mole) of allyl glycidyl ether (Aldrich Chemical Company, Milwaukee, Wis.), and 50.0 g (0.22 mole) of 3-hydro-1,1,1,3,5,5,5-heptamethyltrisiloxane (Hüls Americas, Piscataway, N.J.) in 150 ml of xylene. The addition funnel was charged with a suspension of 2.8 g (0.03 mole) of hexachloroplatinic acid (Aldrich) in 140 ml of n-octyl alcohol. The hexachloroplatinic acid suspension was added drop-wise to the flask, after which the resulting reaction mixture was heated at 100° C.

overnight. The xylene then was removed by rotary evaporation at ambient temperature under reduced pressure. Selective extraction of the residue with hexane yielded the glycidyloxypropylheptamethyltrisiloxane or epoxy trisiloxane (Compound I) after solvent removal. The yield was 68.4 g (94%). The elemental analysis was as follows:

Theoretical: %C, 44.7; %H, 9.3; %Si, 26.8

Found: %C, 44.3; %H, 9.0; %Si, 26.5

The nuclear magnetic resonance data for the product were as follows:

$^1$H NMR (CDCl$_3$): 0.01 (m, Si—CH$_3$), 0.60 (m, Si—CH$_2$—), 3.60 (m,=CH—0),

EXAMPLE 2

Figure 2:
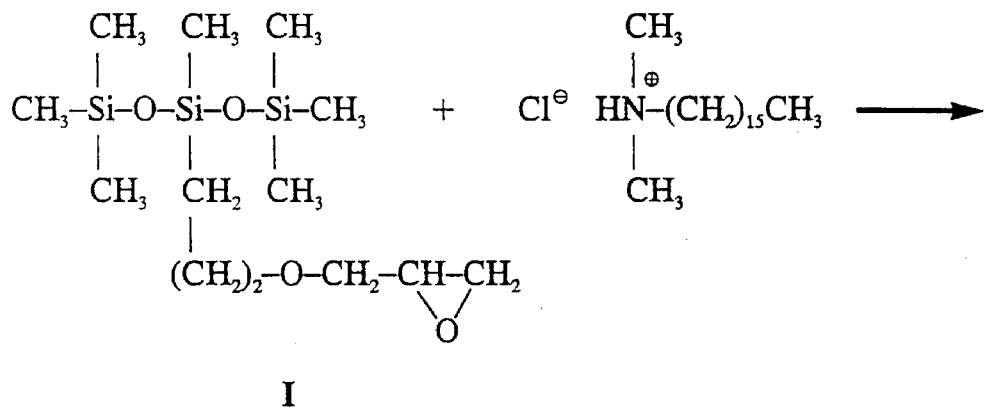
Figure 2:
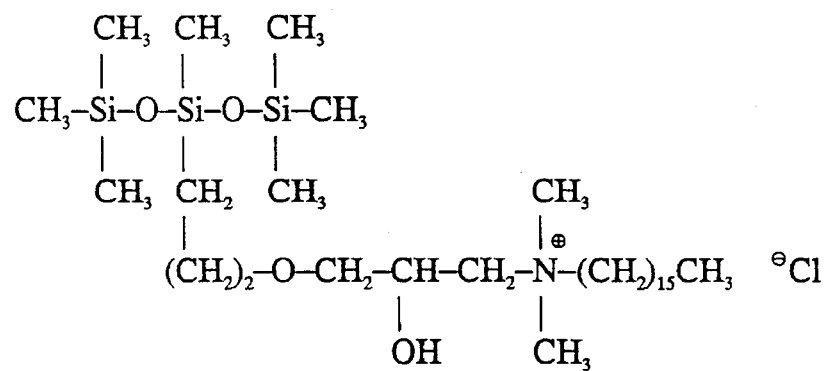

Synthesis of Dimethyl Hexadecyl {2-Hydroxy-3-[3-(1,3,3,3-tetramethyl-1-(trimethylsiloxy)disiloxanyl)-propoxy]propyl} Ammonium Chloride (II) (FIG. 2)

A 500-ml, three-necked, round-bottomed flask was equipped with a stirrer, addition funnel, dry ice/acetone condenser, thermometer and electric heating mantle. The flask was flushed continuously with argon. The flask was charged with 167.2 g (0.55 equivalent) of dimethyl hexadecyl ammonium chloride (Sartomer Chemical Company, West Chester, Pa.), 0.028 g (0.27 milliequivalent) of triethylamine (Aldrich), and 250 g of isopropanol. To the stirred flask contents 65.2 g of the epoxy trisiloxane of Example 1 was added over a ten-minute period. The reaction mixture was stirred and heated at 80° C. for five hours to form a clear solution. The reaction mixture was cooled to ambient temperature and flushed overnight with dry argon. The solvent and other low-boiling materials were removed by rotary evaporation at 45° C. The yield of the quaternary ammonium salt (Compound II), a light yellow oil, was 118 g (87%). The elemental analysis was as follows:

Theoretical: %C, 55.1; %H, 10.7; %Si, 12.6; %N, 2.1

Found: %C, 54.6; %H, 10.4; %Si, 12.1; %N, 1.8

The nuclear magnetic resonance data were as follows:

$^1$H NMR (CDCl$_3$): 0.01 (m, Si—CH$_3$), 0.60 (m, Si—CH$_2$—), 3.60 (m,=CH—0), 2.86 (m,—N—CH$_3$),

EXAMPLE 3

Figure 3:
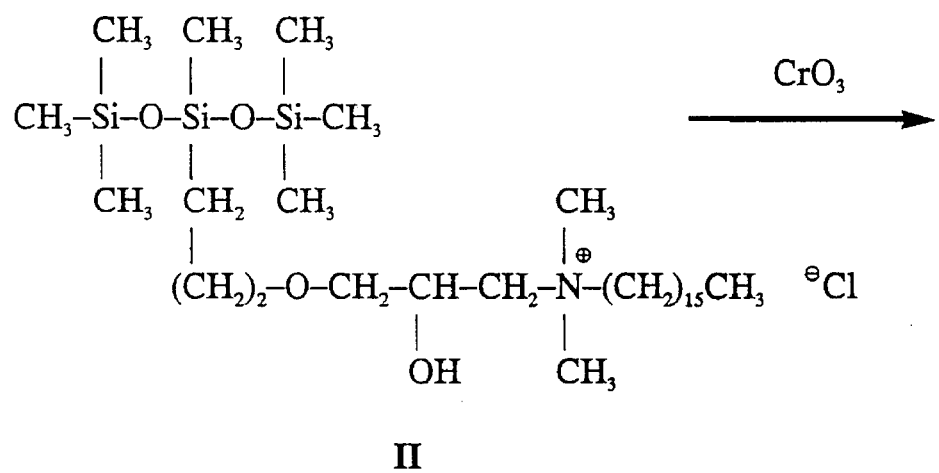
Figure 3:
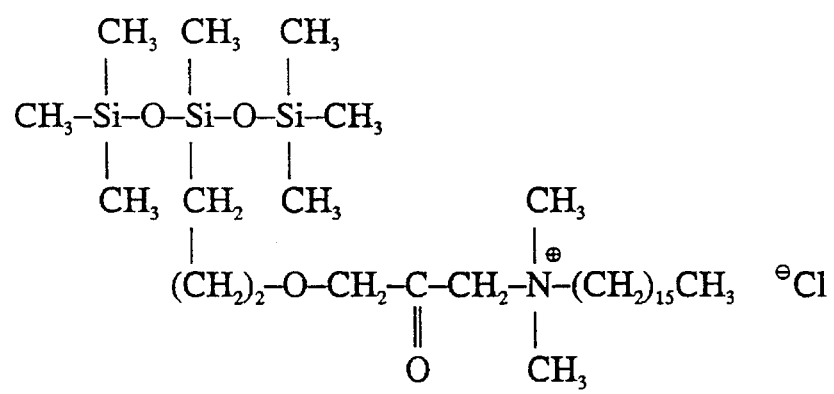

Synthesis of Dimethyl Hexadecyl {3-[3-(1,3,3,3-Tetramethyl-1-(trimethylsiloxy) disiloxanyl)-propoxy]acetonyl} Ammonium Chloride (III) (FIG. 3)

A 250-ml, three-necked, round-bottomed flask was equipped with a stirrer, addition funnel, and condenser. The flask was charged with 14.5 g of chromium trioxide in 100 ml of water. To the flask was added drop-wise 50 g (0.07 mole) of Compound II in 50 ml of tetrahydrofuran. The reaction mixture was stirred overnight and then poured into 200 ml of ice water. The resulting mixture was extracted with diethyl ether. The ether extract was dried and the solvent removed on a rotary evaporator under vacuum to yield 47 g (94%) of Compound III, a light yellow oil. The following elemental analysis was obtained:

Theoretical: %C, 55.3; %H, 10.4; %Si, 12.7; %N, 2.1

Found: %C, 54.7; %H, 10.0; %Si, 12.0; %N, 1.7

An infrared spectrum of the material (neat) showed maxima at 1740 cm$^{-1}$ (C=0) and 1063 cm$^{-1}$ (N—C). The nuclear magnetic resonance data were as follows:

$^1$H NMR (CDCl$_3$): 0.01 (m, Si—CH$_3$), 0.60 (m, Si—CH$_2$—), 3.6 (m,=CH$_2$—0—),

EXAMPLE 4

Figure 4:
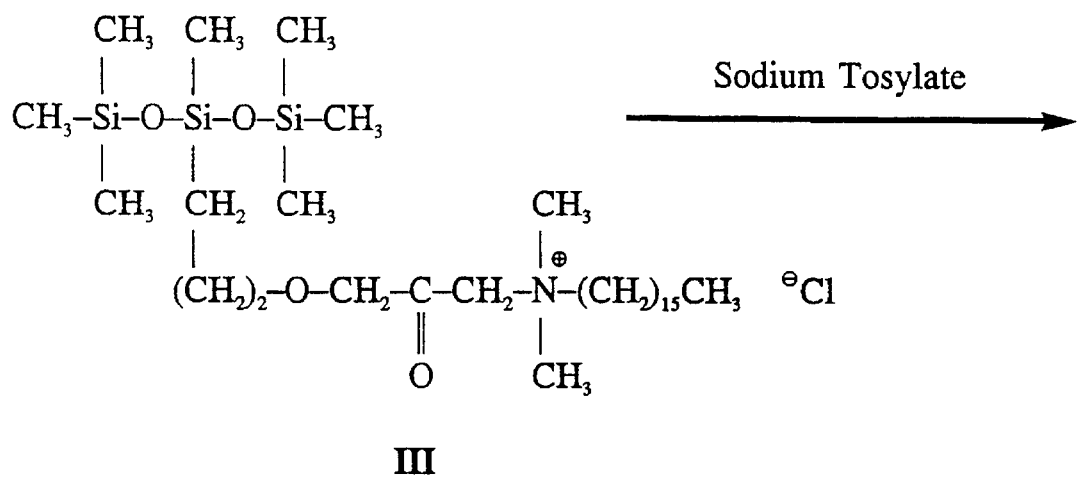
Figure 4:
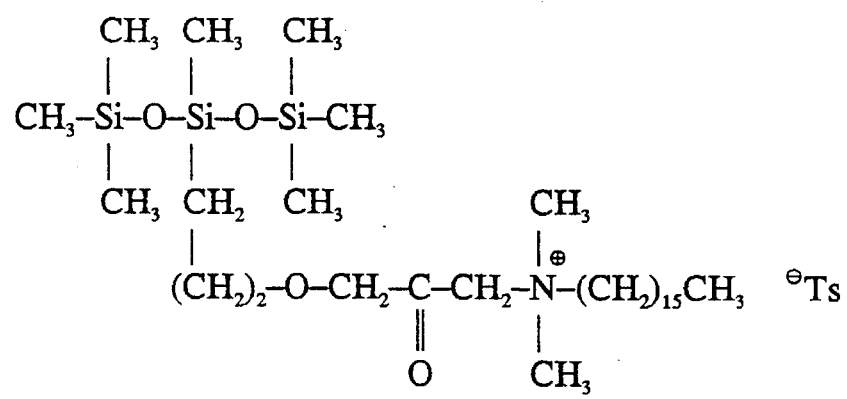

Synthesis of Dimethyl Hexadecyl {3-[3-(1,3,3,3-Tetramethyl-1-(trimethylsiloxy)disiloxanyl)-propoxy]acetonyl} Ammonium p-Toluenesulfonate (IV) (FIG. 4)

A 250-ml, three-necked, round-bottomed flask equipped with a stirrer, addition funnel, and condenser was charged with 50.0 g (74 mmole) of Compound III dissolved in 150 ml of isopropanol. To the solution at ambient temperature was added 57.5 g (0.30 mole) of p-toluenesulfonic acid, sodium salt (Aldrich). The reaction mixture was stirred at ambient temperature for eight hours, after which 50 ml of water was added and the reaction mixture extracted with diethyl ether. Removal of the dried ether extract by rotary evaporation gave 53.4 g (94%) of Compound IV. The following elemental analysis was obtained:

Theoretical: %C, 57.9; %H, 10.3; %Si, 11.2; %S, 4.1; %N, 1.8

Found: %C, 57.6; %H, 10.6; %Si, 11.6; %S, 3.9; %N, 2.1

An infrared spectrum of the material (neat) showed maxima at 1740 cm$^{-1}$ (C=0) and 1063 cm$^{-1}$ (N—C). The nuclear magnetic resonance data for the product were as follows:

$^1$H NMR (CDCl$_3$): 0.01 (m, $^{Si}$—CH$_3$), 0.60 (m, Si—CH$_2$—), 3.6 (m,=CH$_2$—0—),

EXAMPLE 5

Figure 5:
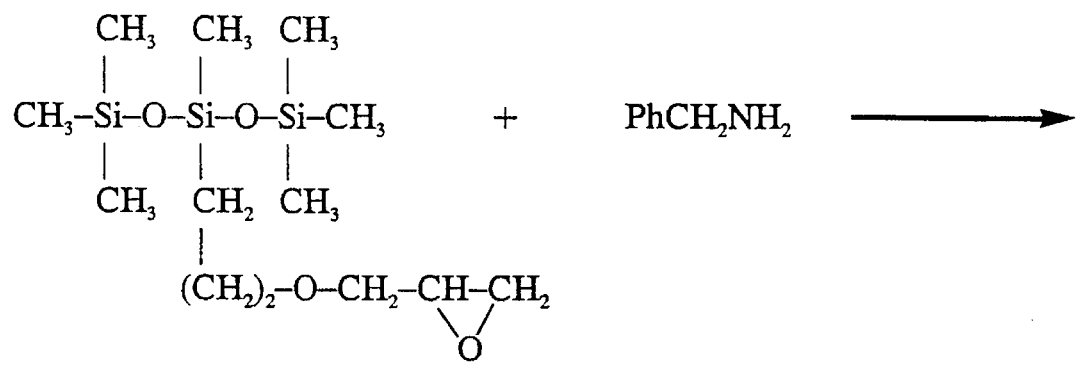
Figure 5:
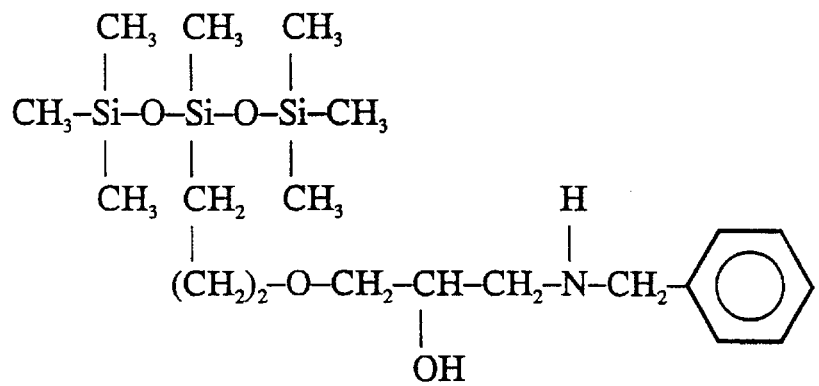

Synthesis of Benzyl-{2-hydroxy-3-[3-(1,3,3,3-tetramethyl-1-(trimethylsiloxy)-disiloxanyl)propoxy]propyl}amine (V) (FIG. 5)

A 500-ml, three-necked, round-bottomed flask equipped with a stirrer, addition funnel, and condenser was charged with 100 g (0.30 mole) of the epoxy trisiloxane (Compound I) of Example 1 dissolved in 200 ml of isopropanol. The addition funnel was charged with a solution of 42.8 g (0.4 mole) of benzylamine (Aldrich) in 100 ml of isopropanol; the solution was added drop-wise to the flask contents at room temperature. The resulting reaction solution was heated at 80° C. for eight hours, after which time the solvent was removed under reduced pressure using a rotary evaporator. The residue, an oil, was passed through a short silica column using 10% ethyl acetate in hexane as eluent. The yield of Compound V, a colorless oil, was 127.8 g (97%). The following elemental analysis was obtained:

Theoretical: %C, 48.7; %H, 9.2; %Si, 18.9; %N, 3.1

Found: %C, 48.4; %H, 9.5; %Si, 18.4; %N, 3.0

An infrared spectrum of the material (neat) showed maxima at 3300 cm$^{-1}$ (OH) and 1063 cm$^{-1}$ (C—N). The nuclear magnetic resonance data were as follows:

$^1$H NMR (CDCl$_3$): 0.01 (m, Si—CH$_3$), 0.60 (m, Si—CH—), 3.6 (m,=CH$_2$—0—), 3.56 (m, Ar—CH$_2$—N)

EXAMPLE 6

Figure 6:
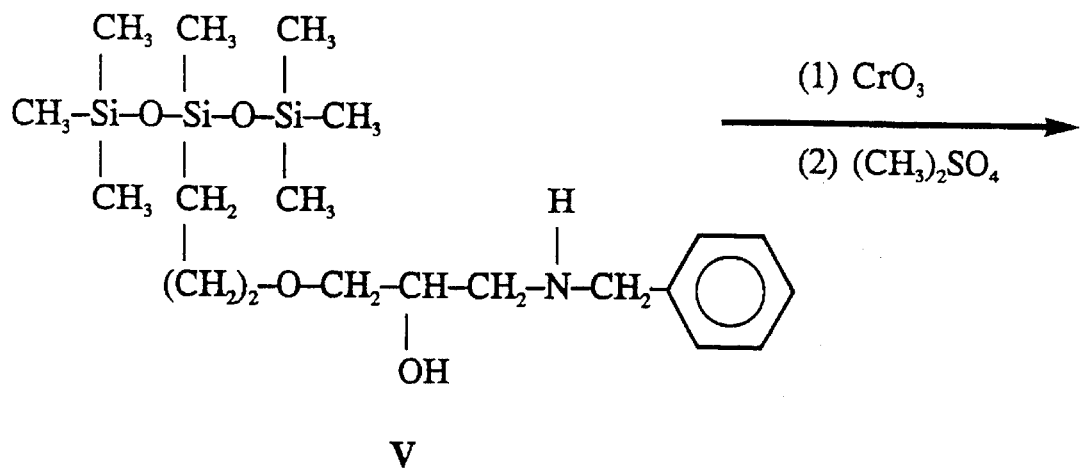
Figure 6:
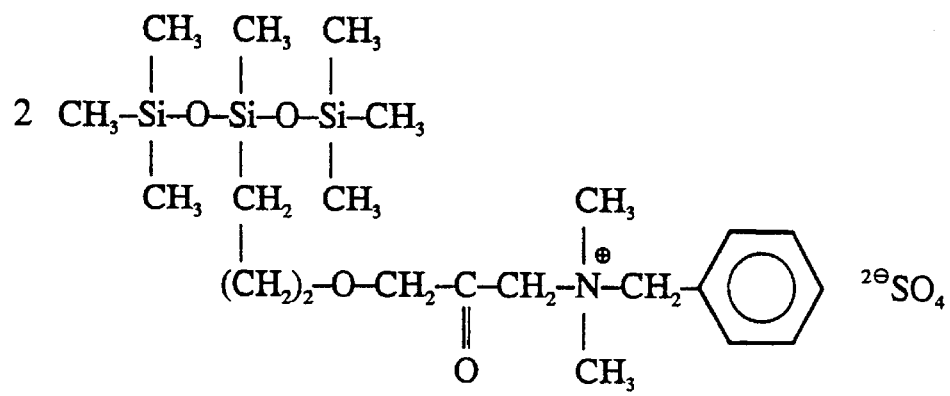

Synthesis of Dimethyl Benzyl {3-[3-(1,3,3,3-Tetramethyl-1-(trimethylisiloxy)disiloxanyl)-propoxy]acetonyl} Ammonium Sulfate (VI) (FIG. 6)

The hydroxy group in Compound V from Example 5 was oxidized to the ketone essentially as described in Example 3. An 80.0-g portion of the resulting ketone was charged to a 500-ml, three-necked, round-bottomed flask fitted with a stirrer, addition funnel, and condenser was added 80.0 g (0.18 mole) of the above ketone product dissolved in 200 ml of dimethyl sulfate (Aldrich). The solution was heated at reflux for eight hours after which the solvent and other volatiles were removed under reduced pressure in a rotary evaporator. The residual oil was passed through a short silica gel column using 30% ethyl acetate in hexane as eluent. Compound VI was obtained as a colorless oil. The yield was 78.4 g (92%). An infrared spectrum of the material (neat) showed a maximum at 1730 cm$^{-1}$ (C=O). The nuclear magnetic resonance data for the product were as follows:

$^1$H NMR (CDCl$_3$): 0.01 (m, Si—CH$_3$), 0.60 (m, Si—CH$_2$—), 2.85 (m,=N—CH$_3$), 3.56 (m, Ar—CH$_2$—N)

EXAMPLE 7

Figure 7:
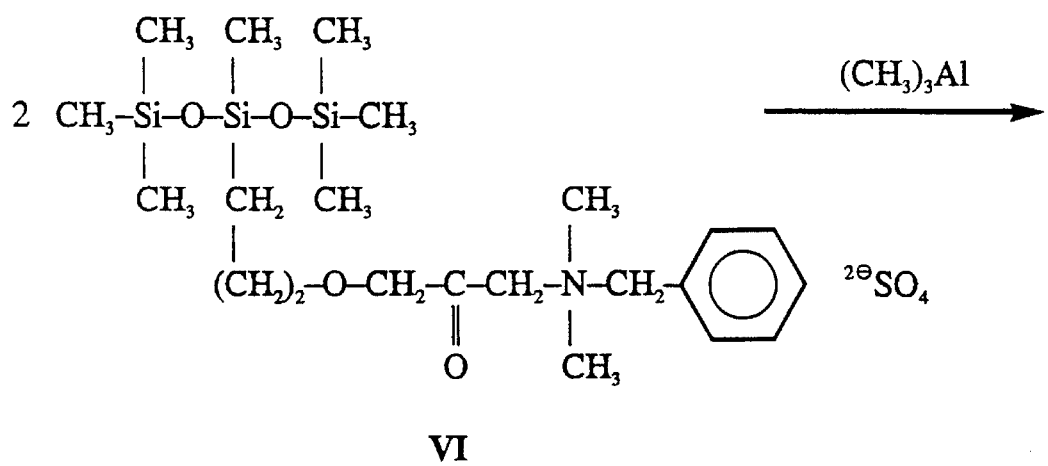
Figure 7:
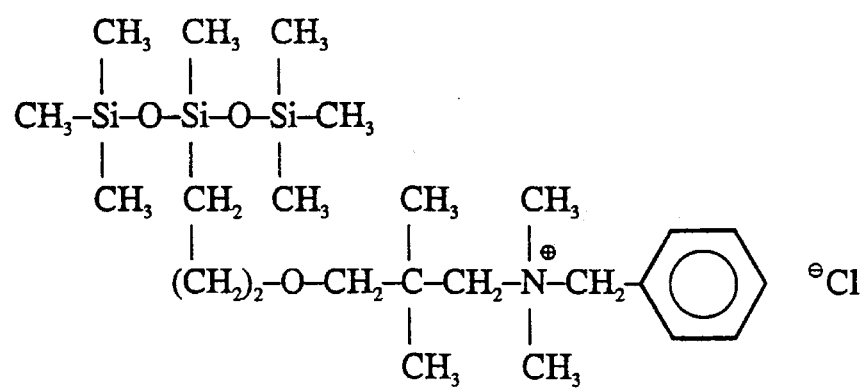

Synthesis of Dimethyl Benzyl {2,2-Dimethyl-3-[3-(1,3,3,3-Tetramethyl-1-(trimethylsiloxy)disiloxanyl)-propoxy]propyl} Ammonium Chloride (VII) (FIG. 7)

In a thick walled glass tube having a sealed bottom were placed 20.0 g (0.04 mole) of Compound VI from Example 6 in 40 ml of benzene (Aldrich), 0.4 ml of water, and 8.6 g (0.12 mole) trimethyl aluminum (Aldrich). The top of the glass tube was sealed and the tube was placed in a stainless steel bomb which was then heated at 140° C. for eight hours. After cooling to ambient temperature, the glass tube was carefully opened and the contents were poured drop-wise into a mixture of 200 ml diethyl ether and 50 ml of 0.5N hydrochloric acid chilled in an ice bath. The organic layer was separated and dried. Solvents were removed under reduced pressure using a rotary evaporator. Compound VII was obtained; the yield was 9.5 g (46%). The nuclear magnetic resonance data for the product were as follows:

$^1$H NMR (CDCl$_3$): 0.01 (m, Si—CH$_3$), 0.60 (m, Si—CH$_2$—), 0.81 (m,≡C—CH$_3$), 2.85 (m,=N—CH$_3$), 3.56 (m, Ar—CH$_2$—N)

EXAMPLE 8

Figure 8:
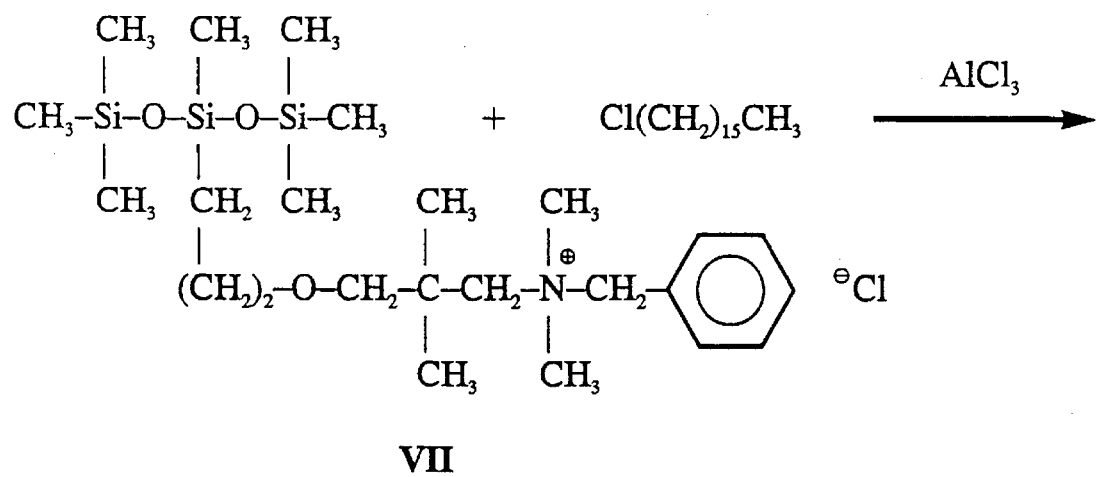
Figure 8:
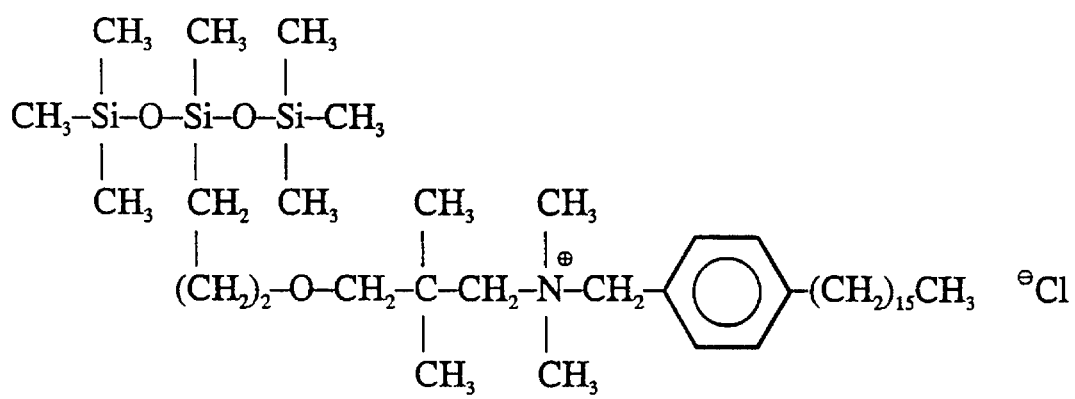

Synthesis of Dimethyl 4-Hexadecylphenylmethyl {2,2-Dimethyl-3-[3-(1,3,3,3-Tetramethyl-1-(trimethylsiloxy)disiloxanyl)-propoxy]propyl} Ammonium Chloride (VIII) (FIG. 8)

To a 500-ml, three-necked, round-bottomed flask fitted with a stirrer, addition funnel, and condenser being continuously flushed with argon was charged 20.0 g (0.04 mole) of Compound VII from Example 7, 15.6 g (0.06 mole) 1-chlorohexadecane (Aldrich), and 200 ml hexane. The resulting reaction mixture was cooled to 0° C. using a crushed ice/salt bath and 2.0 g of anhydrous aluminum chloride was added to the stirred mixture. After 30 minutes an additional 6.0 g of aluminum chloride (0.06 mole total) was added and the reaction mixture slowly heated to 60° C. over a four-hour period. The reaction mixture then was allowed to cool. After cooling, 100 g of crushed ice and 100 ml of water were slowly added. The organic layer was separated and washed with dilute hydrochloride acid, dried and the solvent removed under vacuum on a rotary evaporator. The oil was run through a short silica gel column using 30% ethyl acetate in hexane as eluent. Removal of the solvent gave 23.9 g (82%) of a colorless oil, Compound VIII. The following elemental analysis was obtained:

Theoretical: %C, 62.7; %H, 11.6; %Si, 12.1; %N, 2.0
Found: %C, 62.1; %H, 11.2; %SI, 12.4; %N, 2.4
The nuclear magnetic resonance data were as follows:

$^1$H NMR (CDCl$_3$): 0.01 (m, Si—CH$_3$), 0.60 (m, Si—CH$_2$—), 0.81 (m,≡C—CH$_3$), 2.85 (m,=N—CH$_3$), 3.56 (m, Ar—CH$_2$—N), 6.94 (m, p-substituted benzene)

EXAMPLE 9

Figure 9:
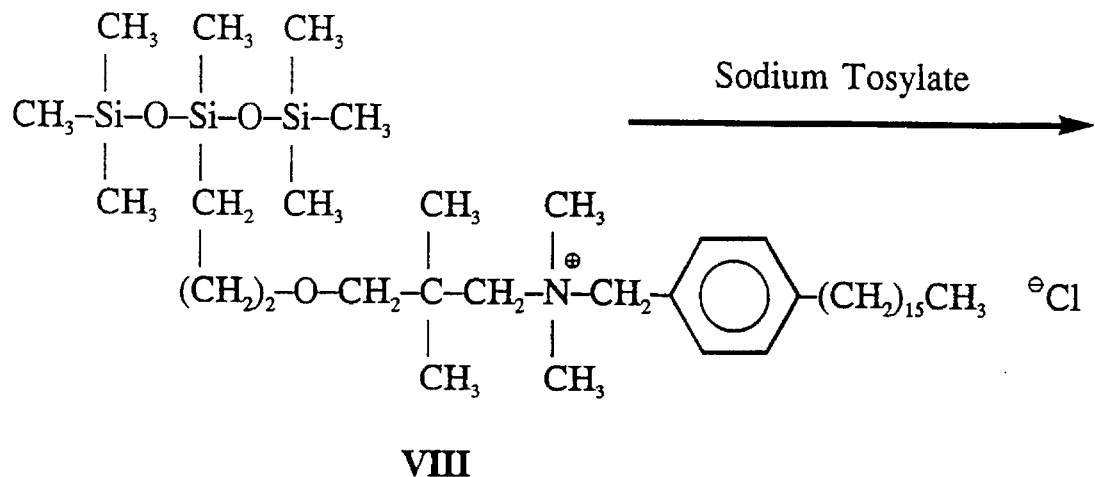
Figure 9:
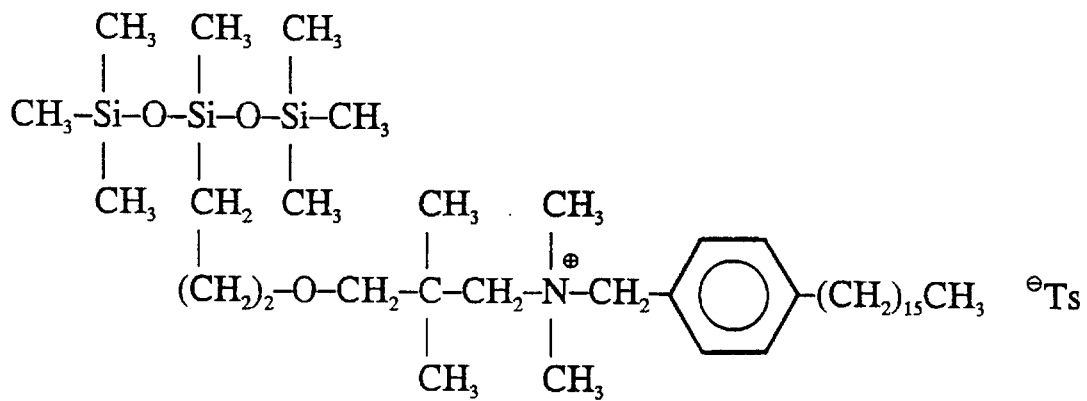

Synthesis of Dimethyl 4-Hexadecylphenylmethyl {2,2-Dimethyl-3-[3-(1,3,3,3-Tetramethyl-1-(trimethylsiloxy)disiloxanyl)-propoxy]propyl} Ammonium p-Toluenesulfonate (IX) (FIG. 9)

The procedure of Example 4 was repeated with Compound VIII. A colorless oil was obtained in 94% yield. The following elemental analysis was obtained:

Theoretical: %C, 59.8; %H, 10.5; %Si, 10.2; %N, 1.7
Found: %C, 59.5; %H, 10.7; %Si, 10.6; %N, 1.4.
The nuclear magnetic resonance data were as follows:

$^1$H NMR (CDCl$_3$): 0.01 (m, Si—CH$_3$), 0.60 (m, Si—CH$_2$—), 0.81 (m,≡C—CH$_3$), 2.85 (m,=N—CH$_3$), 3.56 (m, Ar—CH$_2$—N), 6.94 (m, p-substituted benzene)

EXAMPLE 10

Figure 10:
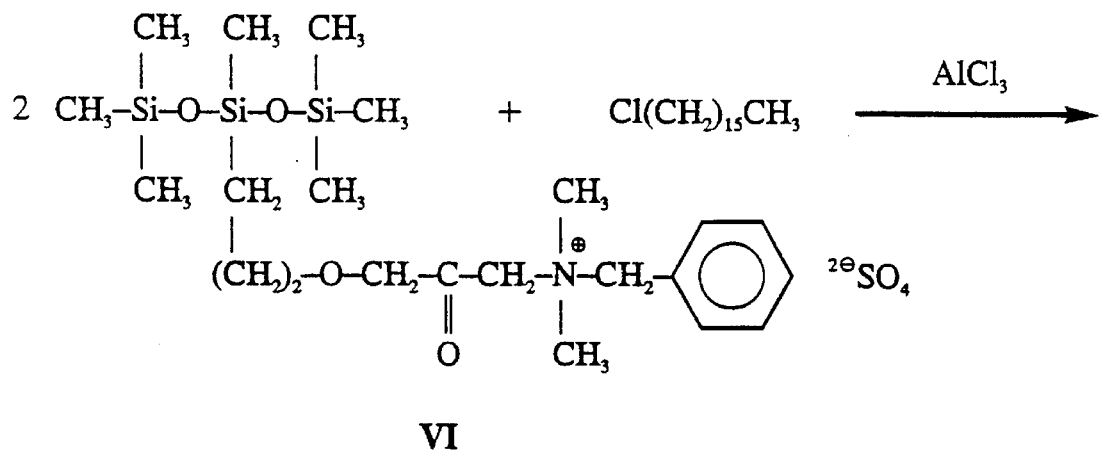
Figure 10:
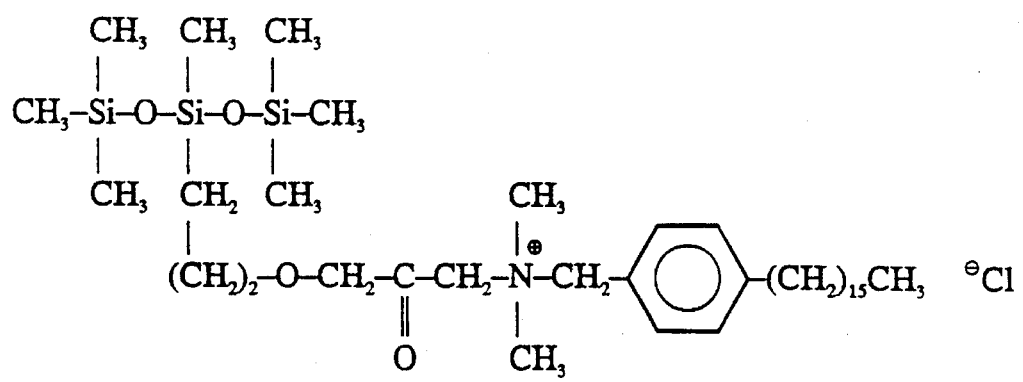

Synthesis of Dimethyl 4-Hexadecylphenylmethyl {3-[3-(1,3,3,3-Tetramethyl-1-(trimethylsiloxy)-disiloxanyl)-propoxy]acetonyl} Ammonium Chloride (X) (FIG. 10)

The procedure of Example 8 was repeated with 20.0 g (0.03 mole) of Compound VI from Example 6 as starting material. The yield of Compound X, a colorless oil, was 21.4 g (81%). The following elemental analysis was obtained:

Theoretical: %C, 62.5; %H, 10.4; %Si, 11.5; %N, 1.9
Found: %C, 62.3; %H, 10.6; %Si, 11.2; %N, 1.7.
The nuclear magnetic resonance data were as follows:

$^1$H NMR (CDCl$_3$): 0.01 (m, Si—CH$_3$), 0.60 (m, Si—CH$_2$—), 2.85 (m,=N—CH$_3$), 3.56 (m, Ar—CH$_2$—N), 6.94 (m. p-substituted benzene)

The antimicrobial activity of five of the compounds of the present invention described in the preceding examples, the thermal stability of such compounds, the preparation of nonwoven webs from thermoplastic compositions which include such antimicrobial compounds, and the biological evaluation of such nonwoven webs are described in the examples which follow.

EXAMPLE 11

Antimicrobial Activities of Various Compounds of the Present Invention

The antimicrobial activities of Compounds II, III, IV, IX, and X were tested at a concentration of $10^{-2}$ g/l. The compound to be tested was added to a 50-ml centrifuge tube containing 100 μ/l of a bacterial stock suspension in which the microorganism concentration was $2.8 \times 10^8$ CFU's/ml. Each tube was maintained at ambient temperature for four hours. At the end of the four-hour period, 30 ml of Letheen broth (Difco, USA) was added to each centrifuge tube. The tubes were vortexed at a setting of 4 G for one minute. The survival of bacteria in the suspension was determined by plating suitable dilutions of sedimented material on Letheen agar (Difco, USA) and counting the number of CFU's after 18 hours of incubation at 37° C. The survival of bacteria was determined by comparing the number of CFU's per ml observed in bacterial suspensions after four hours of incubation in the presence of the test compound and the number of CFU's per ml of the same bacterial suspensions in the control tubes. Such comparisons were done by calculating the log drop for each compound as follows:

Log drop=Log [100–(surviving CFU's/initial CFU's)×100]

See, e.g., R. A. Robison et al., *Appl. Environ. Microbiol.*, 54, 158 (1988). The antibacterial activities of the five compounds are summarized in Table 1.

TABLE 1

Antimicrobial Activity of Five Compounds Reported as Log Drop Values

| | Log Drop of Bacterial Strain | |
|---|---|---|
| Compound | *Escherichia Coli* | *Staphylococcus Epidermidis* |
| II | 3.5 | 4.0 |
| III | 3.5 | 4.1 |
| IV | 3.7 | 4.2 |
| IX | 3.8 | 4.4 |
| X | 3.8 | 4.4 |

As the data in Table 1 show, all five of the compounds possess excellent antibacterial activity.

EXAMPLE 12

Thermal Stability of Five Compounds of the Present Invention

Because the compounds of the present invention are intended to be used in melt-extrusion processes thermal stability is of interest. Accordingly, the thermal stability of each of Compounds II, III, IV, IX, and X was studied. Each compound was placed in a glass tube under a nitrogen atmosphere. The tube was sealed and heated at 232° C. for 30 minutes. The contents of each tube then were analyzed by means of a high pressure liquid chromatography system comprising an ISCO Model 2350 pump, A Waters RCM pack unit containing a Waters C18 5-μ column, a Waters Model 410 differential refractometer, and a Waters Model 745 data module integrator. The solvent employed was deaerated 10 percent water in methanol. The results are summarized in Table 2 which gives the percent decomposition by weight.

TABLE 2

Thermal Stability of Five Compounds Reported as Percent Decomposition by Weight

| Compound | % Decomposition |
|---|---|
| II | 36 |
| III | 32 |
| IV | 8 |
| IX | 1 |
| X | 3 |

The thermal stability of Compounds II and III, while not exceptional, is sufficient to permit the use of the compounds in melt-extrusion processes. This will be especially true in cases where residence times are shorter than 15 minutes and/or extrusion temperatures are lower than 232° C. Because the data in Table 2 resulted from a 30-minute heating period, compound decomposition during melt processing to form nonwoven webs should be less.

Compounds IV, IX, and X, on the other hand, have good to excellent thermal stability. From FIGS. 2, 3, 4, 9, and 10, it is seen that these compounds have fewer β-hydrogen atoms than Compounds II and III and/or the anion is a weak base. These relationships perhaps are best understood by reference to Table 3. Table 3 lists for each of the five compounds the structures associated with the g-carbon atoms, the total number of β-hydrogen atoms, and the anion.

Because there are two β-carbon atoms in each compound, they have been distinguished as follows: the β-carbon atom on the silicon atom side of the nitrogen atom is referred to as being in the "ether moiety," whereas the β-carbon atom on the side "opposite" that of the ether moiety is referred to as being in the "terminal moiety."

TABLE 3

β-Carbon Structures and Anions for Five Compounds of the Present Invention

| | β-Carbon Structure | | | |
|---|---|---|---|---|
| Compound | Ether Moiety | Terminal Moiety | Total β-H's | Anion |
| II | \——CH——<br>\|<br>OH\~ | —CH$_2$— | 3 | Cl$^\ominus$ |
| III | \——C——<br>\|\|<br>O\~ | —CH$_2$— | 2 | Cl$^\ominus$ |
| IV | \——C——<br>\|\|<br>O\~ | —CH$_2$— | 2 | Ts$^\ominus$ |
| IX | CH$_3$<br>\|<br>\——C——\~<br>\|<br>CH$_3$ | \——C≡\~ | 0 | Ts$^\ominus$ |
| X | \——C——<br>\|\|<br>O\~ | \——C≡\~ | 0 | Cl$^\ominus$ |

Thus, compounds having no β-hydrogen atoms and/or a weak base anion represent more thermally stable embodiments.

EXAMPLE 13

Preparation of Polypropylene Spunbonded Webs

Polypropylene nonwoven spunbonded webs were prepared on pilot scale equipment essentially as described in U.S. Pat. No. 4,340,563. The extrusion temperature was approximately 232° C. The process was substantially anaerobic, even though special efforts to exclude oxygen were not taken, and process times typically did not exceed 15 minutes. The webs were thermally point-bonded. The basis weight of each web was 27 g/m$^2$.

A first, negative control web was prepared from polypropylene alone (Web A).

Seventeen webs then were prepared from a mixture of polypropylene and a compound of the present invention (Webs B-R, inclusive). Polypropylene pellets were simply surface-coated with the siloxane quaternary ammonium salt prior to extrusion. After formation and thermal point-bonding, the webs received no further treatment or processing. Five different compounds were evaluated. Each compound was incorporated at three different levels, with two of the compounds being incorporated at a fourth level.

As a second, positive control, a portion of the control web was treated topically with a commercially available siloxane quaternary ammonium salt having the following formula:

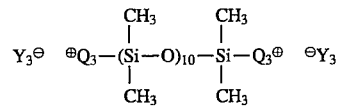

in which $Q_3^{\oplus}$ has the formula,

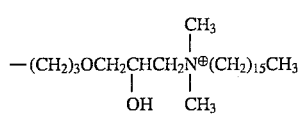

and $^{\ominus}Y_3$ is chloride. The add-on level was 0.9 percent by weight, based on the dry weight of the web (Web S).

The compounds and compound levels employed in the thermoplastic compositions from which nonwoven webs B–R, inclusive, were prepared are summarized in Table 4.

TABLE 4

Compounds and Compound Levels Employed in the Preparation of Webs B–R

| Web | Compound | Compound Level (Weight-Percent) |
|---|---|---|
| B | II | 0.5 |
| C | II | 0.7 |
| D | II | 1.0 |
| E | III | 0.5 |
| F | III | 0.7 |
| G | III | 1.0 |
| H | IV | 0.5 |
| I | IV | 0.7 |
| J | IV | 1.0 |
| K | IX | 0.5 |
| L | IX | 0.7 |
| M | IX | 1.0 |
| N | IX | 1.5 |
| O | X | 0.5 |
| P | X | 0.7 |
| Q | X | 1.0 |
| R | X | 1.5 |

Many of the webs listed in Table 4 were subjected to electron spectroscopy for chemical analysis (ESCA). The ESCA data were collected by Surface Science Laboratories, Inc., Mountain View, Calif., using a Hewlett-Packard 5950 B spectrometer with a monochromatic aluminum K-alpha x-ray source. The scans were done with the open aperture setting for high sensitivity (low resolution). The x-ray power setting was 600–800 watts and charge neutralization was accomplished with a flood gun setting of 13 electron volts. The vacuum utilized was $10^{-8}$ Torr. The area analyzed was about 1×4 mm and the sampling depth was about 100 Å. The results are summarized in Table 5; in the table, atom-% concentration is to a depth of approximately 100 Å.

TABLE 5

ESCA Analysis of Nonwoven Webs

| | Concentration in Atom-% | | | | | |
|---|---|---|---|---|---|---|
| | Found | | | Calculated | | |
| Web | Si | C | N | Si | C | N |
| B | 10.0 | 68.2 | 1.8 | 12.6 | 55.1 | 2.1 |
| D | 10.4 | 67.8 | 1.9 | 12.6 | 55.1 | 2.1 |
| E | 11.0 | 68.0 | 1.9 | 12.7 | 55.3 | 2.1 |
| F | 12.0 | 67.0 | 2.2 | 12.7 | 55.3 | 2.1 |
| G | 12.0 | 66.8 | 1.9 | 12.7 | 55.3 | 2.1 |
| H | 10.0 | 68.0 | 1.5 | 11.2 | 57.9 | 1.8 |
| J | 10.5 | 67.8 | 1.6 | 11.2 | 57.9 | 1.8 |
| K | 10.0 | 62.4 | 1.5 | 10.2 | 59.8 | 1.7 |
| M | 10.0 | 62.6 | 1.6 | 10.2 | 59.8 | 1.7 |
| N | 10.0 | 62.4 | 1.6 | 10.2 | 59.8 | 1.7 |
| O | 11.5 | 64.4 | 1.8 | 12.1 | 61.2 | 2.0 |
| Q | 11.8 | 65.2 | 1.9 | 12.1 | 61.2 | 2.0 |

TABLE 5-continued

ESCA Analysis of Nonwoven Webs

| | Concentration in Atom-% | | | | | |
|---|---|---|---|---|---|---|
| | Found | | | Calculated | | |
| Web | Si | C | N | Si | C | N |
| R | 12.0 | 64.6 | 1.9 | 12.1 | 61.2 | 2.0 |
| S | 14.0 | 65.0 | 2.3 | — | — | — |

It is evident from Table 5 that a substantial portion of the surfaces of the fibers of the nonwoven webs studied consists of the antimicrobial compound present in the thermoplastic composition from which the webs were prepared. That is, the compounds of the present invention appear to have surface segregated to a remarkable and unexpected degree.

In an effort to aid in the visualization of the effectiveness or completeness of such surface segregation, the ratios of silicon found to theoretical silicon and nitrogen found to theoretical nitrogen were calculated from the data in Table 5 as follows:

Si=100×(silicon conc'n. found/theoretical silicon conc'n.)

N=100×(nitrogen conc'n. found/theoretical nitrogen conc'n.)

Thus, the calculations give the ESCA value of either silicon or nitrogen as a percentage of the theoretical value for that element. These calculations are summarized in Table 6, which also includes the data from Table 4 for convenience.

TABLE 6

Silicon and Nitrogen Ratios from ESCA Data

| | Compound and Level | | Found: Calc'd. Ratios | |
|---|---|---|---|---|
| Web | Compound | Weight-% | Silicon | Nitrogen |
| B | II | 0.5 | 79 | 86 |
| D | II | 1.0 | 83 | 90 |
| E | III | 0.5 | 87 | 90 |
| F | III | 0.7 | 94 | 100 |
| G | III | 1.0 | 94 | 90 |
| H | IV | 0.5 | 89 | 83 |
| J | IV | 1.0 | 94 | 89 |
| K | IX | 0.5 | 98 | 88 |
| M | IX | 1.0 | 98 | 94 |
| N | IX | 1.5 | 98 | 94 |
| O | X | 0.5 | 95 | 90 |
| Q | X | 1.0 | 98 | 95 |
| R | X | 1.5 | 99 | 95 |

Figure 11:
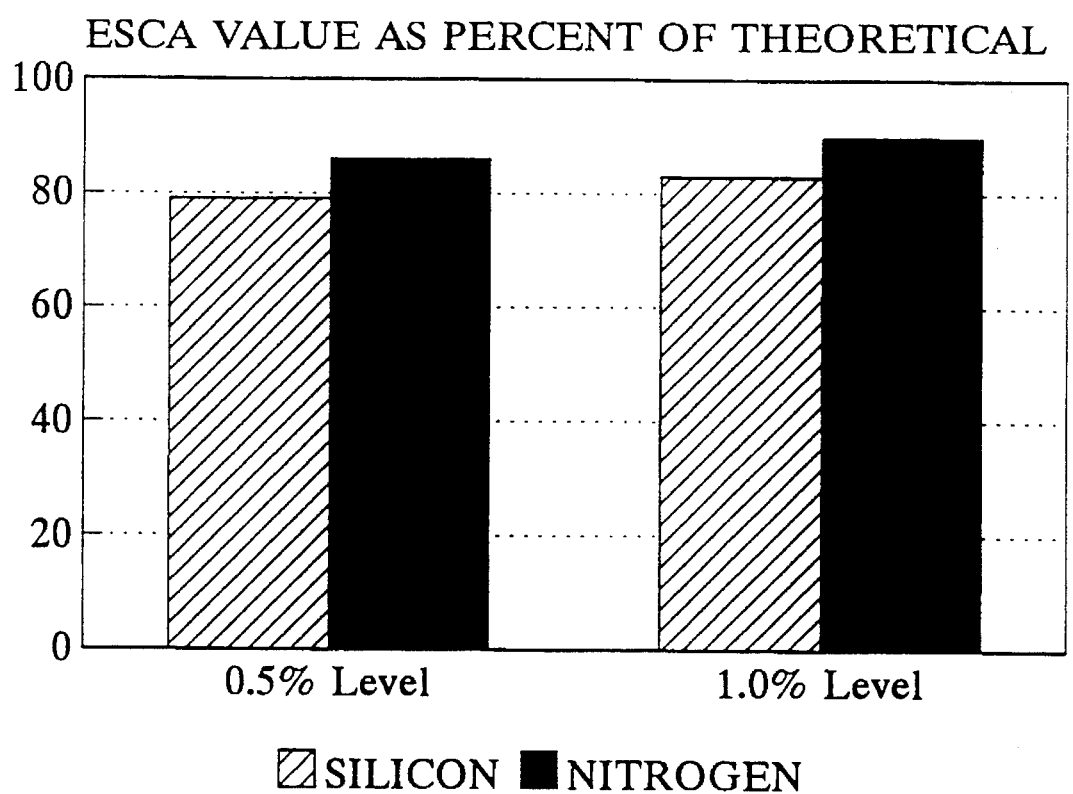
FIGS. 11–15 are bar graphs of ESCA values for silicon and nitrogen, expressed as percentages of the theoretical values, of antimicrobial nonwoven webs prepared in accordance with the present invention.
Figure 12:
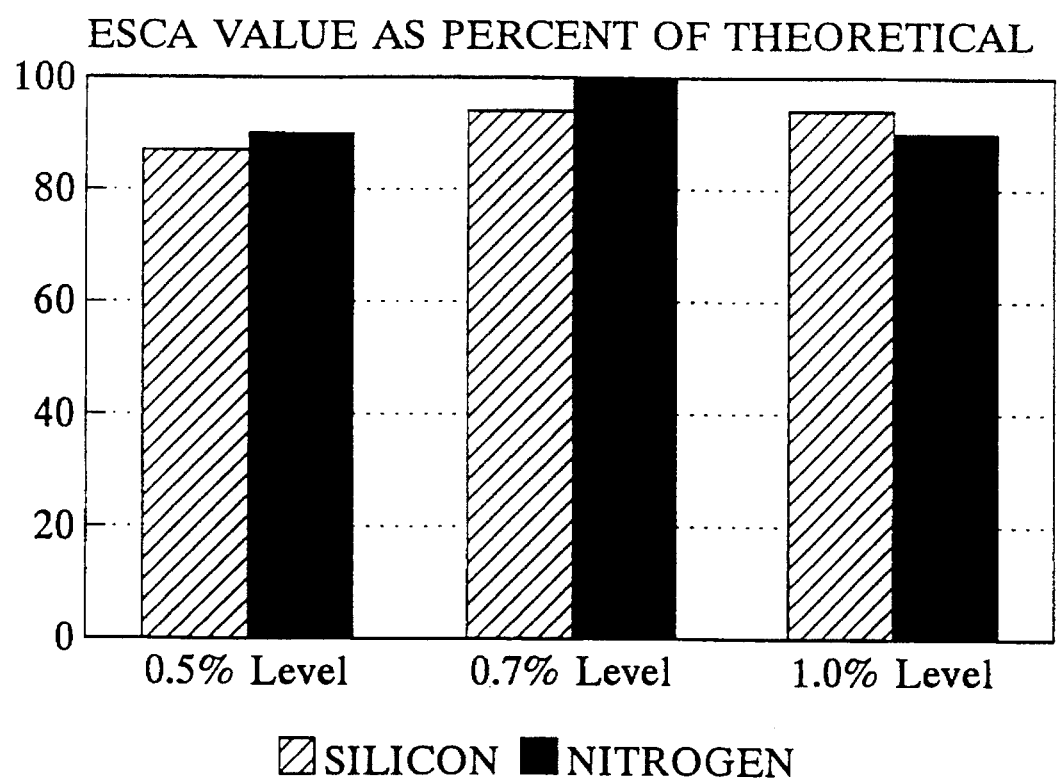
Figure 13:
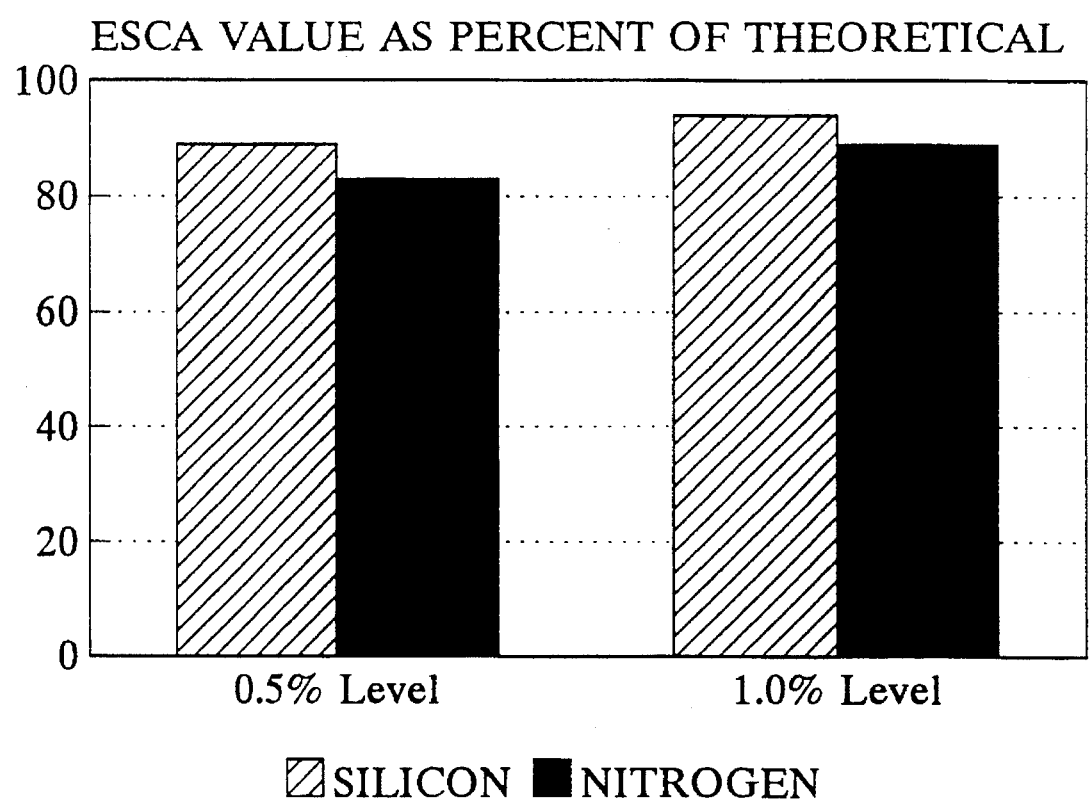
Figure 14:
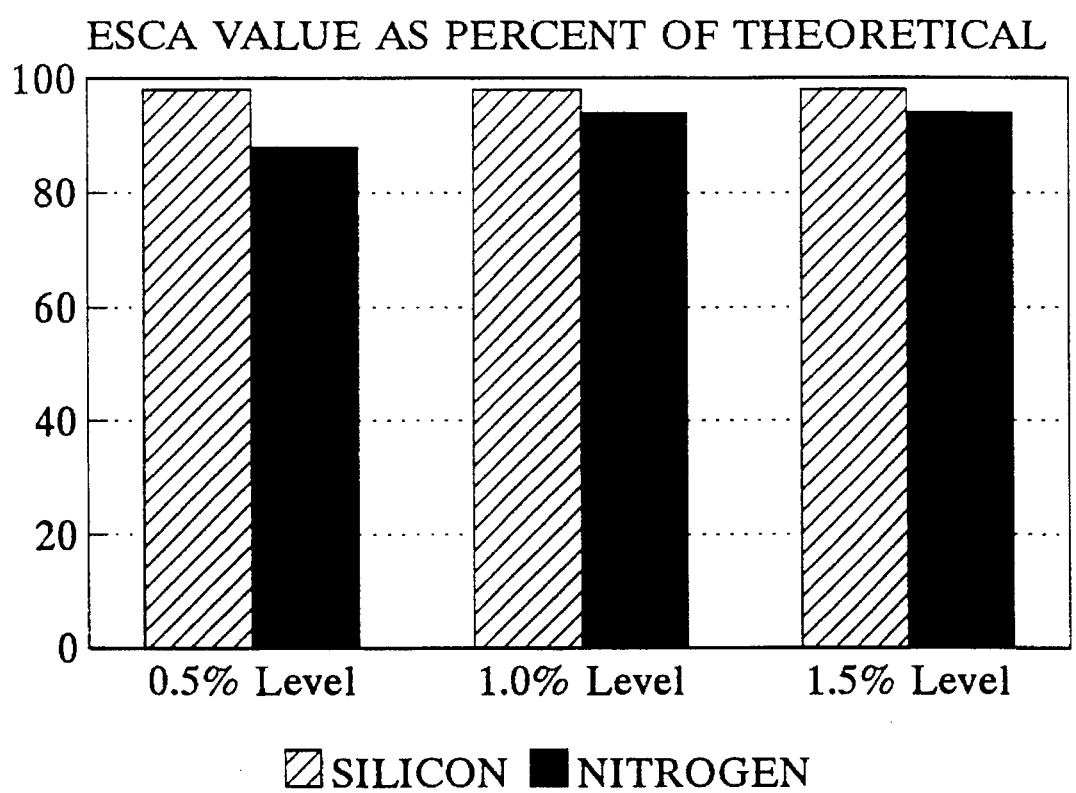
Figure 15:
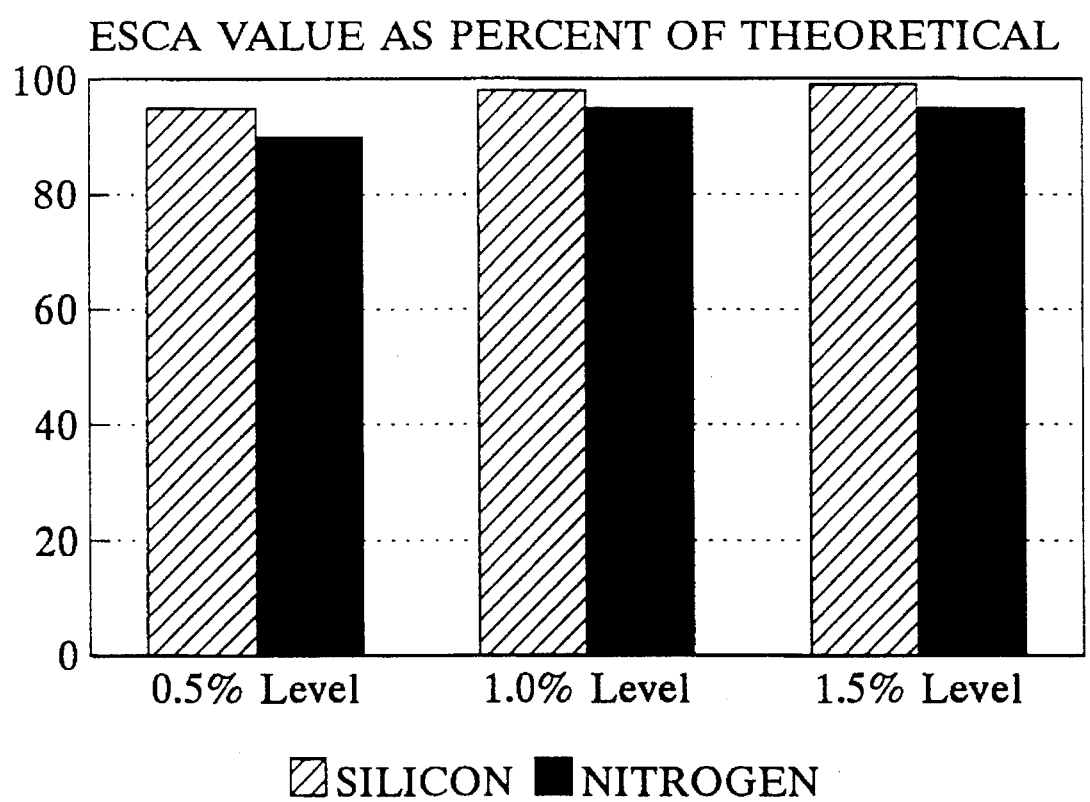

The data in Table 6 were plotted as bar graphs, grouped by compound number, and are presented as FIGS. 11–15, inclusive. Thus, FIG. 11 is a bar graph of the silicon and nitrogen ESCA values for Compound II at levels of 0.5% and 1.0% by weight, expressed as a percentage of the theoretical values, i.e., the data for webs B and D. FIG. 12 is a bar graph of the data for webs E, F, and G; FIG. 13 is a bar graph of the data for webs H and J; FIG. 14 is a bar graph of the data for webs K, M, and N; and FIG. 15 is a bar graph of the data for webs O, Q, and R.

The basis for the statement above that the compounds of the present invention surface segregate to a remarkable and unexpected degree is clear from Table 6 and FIGS. 11–15. If the surfaces of the fibers of the nonwoven webs were completely covered by or with an antimicrobial compound of the present invention, the ESCA values for silicon and nitrogen would be equal to the theoretical values. Stated differently, the ESCA values would be equal to the theoretical values if the antimicrobial compound were present on the surfaces of the fibers to an approximate depth of 100 ÅA. Even with the experimental error inherent in ESCA analyses, the 100-Å portion of the fiber surfaces measured by ESCA consist essentially of antimicrobial compound. Equally significant is the fact that essentially complete coverage of the fiber surfaces was obtained with several compounds even at levels of 0.5 percent by weight. For those compounds, it is evident that lower levels can be used without sacrificing the antimicrobial activity of the nonwoven webs.

The fact that the antimicrobial compounds are found in such high concentrations to a depth of 100 Å (and possibly deeper) strongly suggests that the antimicrobial properties demonstrated to be present at the surfaces of the fibers are likely to be durable. That is, such compounds form an extended antimicrobial surface, i.e., an antimicrobial surface which extends below the air/fiber interfacial surface. Because of the high concentrations of anti-microbial compounds near (i.e., within 100 Å of) the fiber interfacial surfaces, compound which may be removed from the interfacial surface by dissolution in a solvent or other process can be replenished from the extended surface reservoir of antimicrobial compound.

EXAMPLE 14

Antimicrobial Activities of the Nonwoven Webs of Example 13

The bacterial strains *Escherichia coli* (ATCC No. 13706) and *Staphylococcus epidermidis* (ATCC No. 1859) were used to evaluate the antibacterial activity of the nonwoven webs prepared in Example 13. Bacterial suspensions containing about $10^8$ colony forming units (CFU's) per ml were obtained by collecting overnight growth from tryptic soy agar (Difco, USA) in saline.

Each web was cut into 1"×1" (about 2.5 cm×2.5 cm) samples. Each sample was placed in a 50-ml centrifuge tube, to which was added 100 µl of a bacterial stock suspension containing $2.8 \times 10^8$ CFU's/ml. Samples were left at ambient temperature for four hours. At the end of the four-hour period, 30 ml of Letheen broth (Difco, USA) was added to each centrifuge tube. The tubes were vortexed at a setting of 4 G for one minute. The survival of bacteria in the presence of the nonwoven web was determined as described in Example 11. The antibacterial activities of the webs of Example 13 are summarized in Table 7.

TABLE 7

Antibacterial Activities of the
Nonwoven Webs of Example 13
Reported as Log Drop Values

| | Log Drop Values for Bacterial Strain | |
|---|---|---|
| Web | *Escherichia Coli* | *Staphylococcus Epidermidis* |
| A | No Change | No Change |
| B | 1.2 | 1.9 |
| C | 1.2 | 1.9 |
| D | 1.8 | 2.2 |
| E | 1.6 | 2.2 |
| F | 1.6 | 2.2 |
| G | 1.8 | 2.3 |
| H | 3.1 | 3.8 |
| I | 3.1 | 3.8 |
| J | 3.5 | 4.0 |
| K | 3.8 | 4.4 |
| L | 3.8 | 4.4 |

TABLE 7-continued

Antibacterial Activities of the
Nonwoven Webs of Example 13
Reported as Log Drop Values

| | Log Drop Values for Bacterial Strain | |
|---|---|---|
| Web | *Escherichia Coli* | *Staphylococcus Epidermidis* |
| M | 4.0 | 4.5 |
| N | 4.1 | 4.5 |
| O | 3.8 | 4.4 |
| P | 3.8 | 4.4 |
| Q | 4.1 | 4.5 |
| R | 4.1 | 4.5 |
| S | 0.9 | 1.6 |

Figure 16:
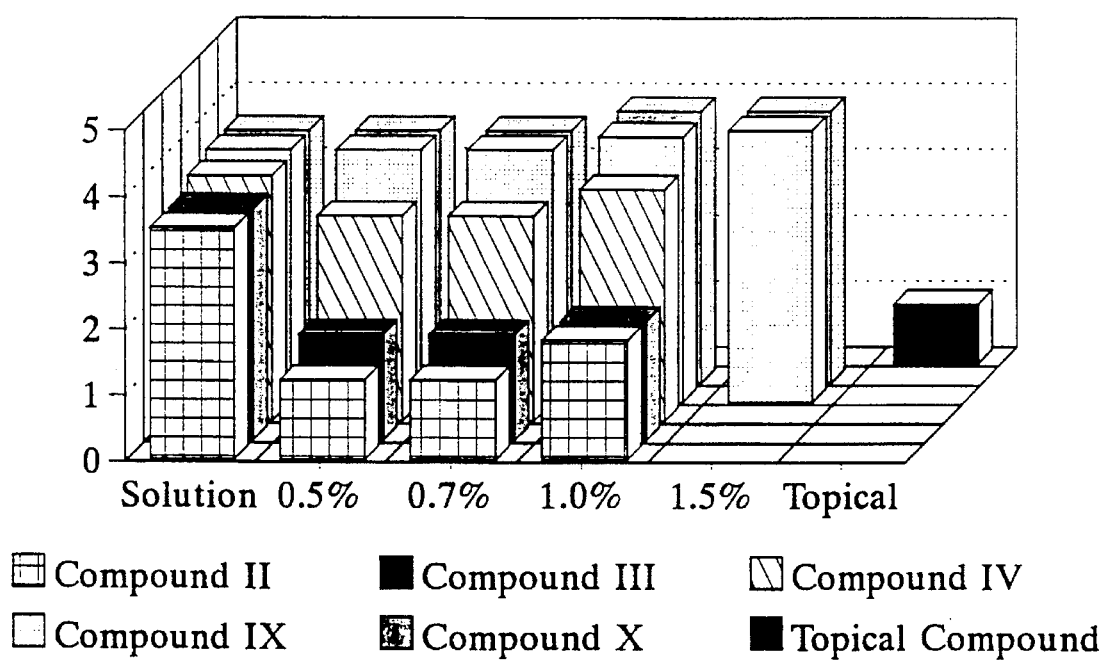
FIGS. 16 and 17 are three-dimensional bar graphs of log drop data for two microorganisms exposed to antimicrobial nonwoven webs prepared in accordance with the present invention.
Figure 17:
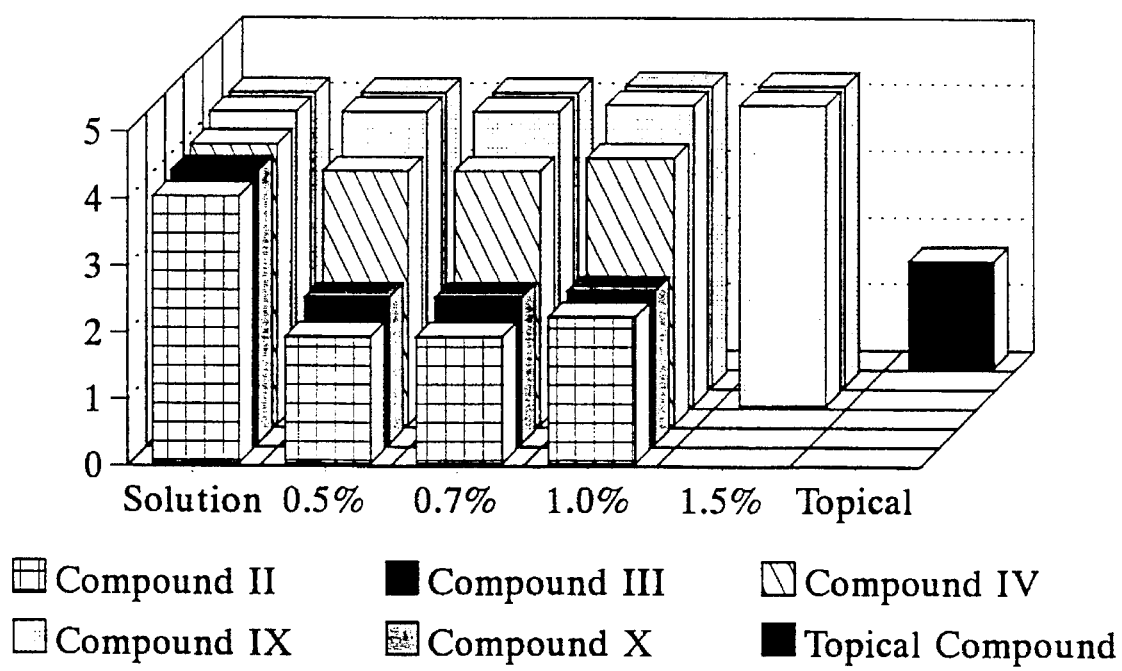

A careful study of the data in Table 7 makes it clear that the compounds previously demonstrated to be at the surfaces of the fibers making up the nonwoven webs are effective as antimicrobial agents. In order to assist in the visualization and appreciation of the data, however, two bar graphs were prepared and are included as FIGS. 16 and 17. FIG. 16 is a three-dimensional bar graph of the log drop data for *Escherichia coli*, with the data being grouped by compound level; the figure also includes the log drop data for the compounds in solution and the topically applied compound. FIG. 17 is similar to FIG. 16, except that the log drop data are for *Staphylococcus epidermidis*.

FIGS. 16 and 17, in conjunction with Table 7, clearly support at least the following conclusions:

(1) all of the internally incorporated compounds resulted in fibers having antimicrobial activity as good as or better than the topically applied compound;

(2) of the five compounds investigated as internal additives, Compounds IV, IX, and X were more effective in imparting antimicrobial properties to the surfaces of the fibers;

(3) Compound IV was almost as effective as an internal additive as when used in solution;

(4) Compounds IX and X were as effective or more effective as internal additives as when used in solution; and (5) the effectiveness of Compounds IX and X as internal additives does not appear to be concentration dependent at the levels studied.

Two particularly interesting aspects of FIGS. 16 and 17 are worthy of further comment. First, FIGS. 16 and 17 dramatically illustrate the relatively constant high effectiveness of Compounds IX and X. Consequently, levels of these compounds below 0.5 percent by weight clearly can be used. Based on the increases in effectiveness with increasing concentration of all five compounds, levels as low as 0.1 percent by weight should be feasible. Depending on the level of antimicrobial activity desired, even lower levels probably can be used. Although levels above 1.5 percent by weight also can be used, significant increases in antimicrobial activity would not be expected. However, such higher levels may be useful in instances where it is desired to provide a reservoir of antimicrobial compound at the surfaces of the fibers of the nonwoven webs. Thus, levels of from about 0.1 to about 3 percent by weight represent a practical range.

Second, the increases in log drop for Compounds II, III, and IV are generally similar. Moreover, the antimicrobial effectiveness of each of these compounds when incorporated into a nonwoven web appears to be directly proportional to the thermal stability of the compound. That is, the compounds having higher thermal decomposition also resulted in lower antimicrobial activity, even though such activity still is equal to or greater than the activity of the topically applied compound.

The antimicrobial activity of the compounds, when incorporated into nonwoven webs, is less than what have been expected, based only on the ESCA analyses; compare FIGS. 11–13 with FIGS. 16 and 17 (or compare Tables 5 and 6 with Table 7). This is particularly true for compounds II and III. While the ESCA analyses gave values for silicon and nitrogen which were at least 80 percent of the theoretical values, the differences in log drop values were much greater. For example, the log drop values for Compound II with *E. coli* and *S. epidermidis* were 3.5 and 4.0 respectively (see Table 1). The corresponding log drop values obtained upon incorporating Compound II into the fibers of a nonwoven web, however, were lower by approximately 2 (1.7–2.3 and 1.8–2.1, respectively). The log drop values for Compound III with *E. coli* and *S. epidermidis* were 3.5 and 4.1 respectively (see Table 1). The corresponding log drop values obtained upon incorporating Compound III into the fibers of a nonwoven web also were lower by approximately 2 (1.7–1.9 and 1.8–1.9, respectively). Since each log drop unit represents a ten-fold difference, the lower log drop values just described represent an approximately 100-fold difference.

The explanation for the apparent anomaly between the antimicrobial effectiveness observed upon incorporating Compounds II and III into nonwoven webs and the ESCA data is believed to be based on the nature of the products which result upon the thermal degradation of these compounds. Based on thermogravimetric analyses or TGA (not reported), it was determined that the compounds of the present invention in general did not undergo significant weight loss upon being heated to approximately 230° C. From the results described in Example 12, it is clear that Compounds II and III do, in fact, experience some thermal degradation. Because of the TGA results, however, it appears that the thermal degradation products are not significantly volatile under the conditions encountered in the melt-extrusion process, even though no attempt was made to characterize or identify such products. It is assumed, therefore, that such products are at least in part carried to the surfaces of the fibers, or that degradation occurs at the surfaces of the fibers, and such products lack antimicrobial properties sufficient to have an effect upon the antimicrobial effectiveness of the nonwoven webs. However, the presence of degradation products at the surfaces of the fibers still would contribute to the silicon and nitrogen values observed by ESCA analyses. FIGS. 16 and 17 make it clear that the effect of thermal degradation, whenever it occurs, can be partially offset by increasing the level of the compound in the thermoplastic composition from which the nonwoven web is prepared. Whenever permitted by process requirements, reducing melt extrusion temperatures and/or residence times in the melt will contribute to reducing the extent of thermal degradation.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for preparing a nonwoven web having antimicrobal properties which comprises:

melting a melt-extrudable thermoplastic composition:

extruding the molten composition through multiple orifices to form streams of molten composition;

cooling the streams of molten composition to form fibers; and randomly depositing said fibers on a moving foraminous surface to form a web; wherein said melt-extrudable thermoplastic composition at least one thermoplastic polyolefin which contains only hydrogen and carbon atoms and at least one additive which is adapted to surface segregate upon extrusion of the molten composition to impart antimicrobial properties to the surface of said fibers of which said nonwoven web is comprised wherein said additive has either the general formula A,

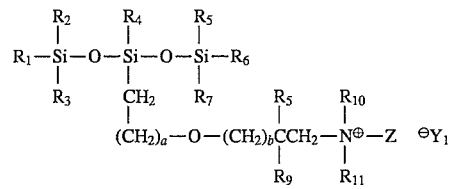

wherein:

(1) each of $R_1$–$R_7$ is independently selected from the group consisting of monovalent $C_1$–$C_{20}$ alkyl, phenyl, and phenyl-substituted $C_1$–$C_{20}$ alkyl groups, in which each phenyl can be substituted or unsubstituted;

(2) each of $R_8$ and $R_9$ is a monovalent group independently selected from the group consisting of (a) hydrogen and (b) monovalent alkyl, cycloalkyl, aryl, and heterocyclic groups and combinations thereof having up to about 30 carbon atoms, except that both $R_8$ and $R_9$ cannot be hydrogen; or, when taken together in combination with the carbon atom to which they are attached, $R_8$ and $R_9$ represent a carbonyl group;

(3) each of $R_{10}$ and $R_{11}$ is a methyl group;

(4) a represents an integer from 1 to about 20;

(5) b represents an integer from 1 to about 20;

(6) Z is a monovalent group having from about 8 to about 30 carbon atoms and selected from the group consisting of alkyl, cycloalkyl, aryl, and heterocyclic groups, and combinations thereof, wherein Z is terminated by an alkyl moiety which includes at least about 8 carbon atoms in a single continuous chain;

(7) $Y_1$ is an anion which does not cause the thermal instability of the additive to be more than about 35 wt. % decomposition during melt extrusion; and (8) said additive has a molecular weight of from about 600 to about 1,700; or the general formula B,

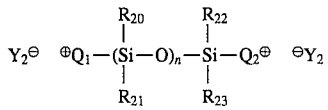

wherein:
(1) each of $R_{20}$–$R_{23}$ is independently selected from the group consisting of monovalent $C_1$–$C_{20}$ alkyl, phenyl, and phenyl-substituted $C_1$–$C_{20}$ alkyl groups, in which each phenyl can be substituted or unsubstituted;
(2) n represents an integer of from 1 to about 19;
(3) each of $Q_1$ and $Q_2$ represents an independently selected quaternary ammonium group having the general formula,

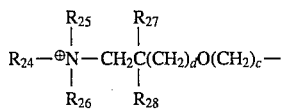

in which:
(a) $R_{24}$ is a monovalent alkyl group having from about 8 to about 30 carbon atoms, at least about 8 carbon atom of which make up a single continuous chain;
(b) $R_{25}$ and $R_{26}$ are methyl groups;
(c) each of $R_{27}$ and $R_{28}$ is a monovalent group independently selected from the group consisting of (i) hydrogen and (ii) monovalent alkyl, cycloalkyl, aryl, and heterocyclic groups and combinations thereof having up to about 30 carbon atoms, except that both $R_{27}$ and $R_{28}$ cannot be hydrogen; or, when taken together in combination with the carbon atom to which they are attached, $R_{27}$ and $R_{28}$ represent a carbonyl group;
(d) c represents an integer of from 2 to about 20; and
(e) d represents an integer of from 2 to about 20;
(4) $Y_2$ represents an anion which does not cause the thermal instability of the additive to be more than about 35 wt. % decomposition during melt extrusion; and
(5) said additive has a polydispersity of up to about 3.0 and a weight-average molecular weight of from about 800 to about 2,000;

wherein said additive is present in said melt-extrudable thermoplastic composition in an amount sufficient to impart antimicrobial activity to the surfaces of said fibers of which said nonwoven web is comprised.

2. The method of claim 1, in which said thermoplastic polyolefin is polyethylene or polypropylene.

3. The method of claim 1, in which Z is a monovalent group having the general formula,

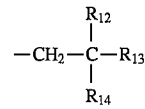

in which each of $R_{12}$–$R_{14}$ is an independently selected monovalent alkyl group wherein the total number of carbon atoms in all of $R_{12}$–$R_{14}$ is from about 6 to about 28 and at least one of $R_{12}$–$R_{14}$ contains at least about 6 carbon atoms in a single continuous chain.

4. The method of claim 1, in which Z is a monovalent group having the general formula,

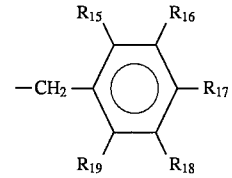

in which each of $R_{15}$–$R_{19}$ is a monovalent group independently selected from the group consisting of hydrogen and alkyl, and wherein the total number of carbon atoms in all of $R_{15}$–$R_{19}$ is from about 8 to about 23, with at least one of $R_{15}$–$R_{19}$.

5. The method of claim 4, in which each of $R_{15}$, $R_{16}$, $R_{18}$, and $R_{19}$ is hydrogen and $R_{17}$ is hexadecyl.

6. The method of claim 1, in which each of $Y_1$ and $Y_2$ independently is selected from the group consisting of a weak base.

7. The method of claim 1, in which said additive has the formula,

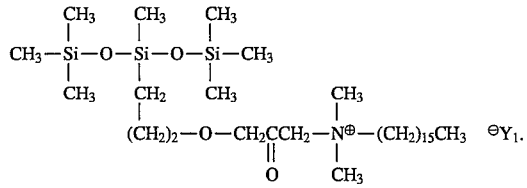

8. The method of claim 1, in which said additive has the formula,

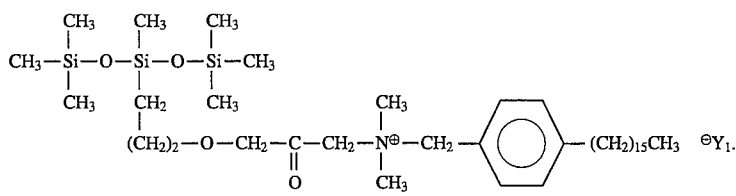

9. The method of claim 1, in which said additive has the formula,

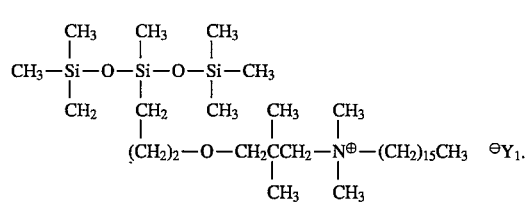

* * * * *

UNITED STATES PATENT AND TRADEMARK OFFICE
CERTIFICATE OF CORRECTION

PATENT NO. : 5,567,372

DATED : October 22, 1996

INVENTOR(S) : Ron S. Nohr, et al.

It is certified that error appears in the above-indentified patent and that said Letters Patent is hereby corrected as shown below:

Column 2, line 52, "$R^5$" should read --$R^8$--;
Column 6, line 55, "$R^5$" should read --$R^8$--;
Column 12, line 34, "SchwarzkopfMicroanalytical" should read --Schwarzkopf Microanalytical--;
Column 14, line 54, "Si—CH—)" should read --Si—$CH_2$—)--;
Column 15, line 29, "0.5N" should read --0.5 N--;
Column 17, line 60, "IV." should read --IV,--;
Column 17, line 66, "g-carbon" should read --ß-carbon--;
Column 18, line 42, "4,340,563" should read --4,360,563--;
Column 24, line 13, "composition:" should read --composition;--;
Column 24, line 21, "composition at" should read --composition comprises at--;
Column 24, line 34, "$R^5$" should read --$R^8$--;
Title page, under "Other Publications", last reference, "Robinson" should read --Robison--.

Signed and Sealed this

Twenty-fourth Day of June, 1997

Attest:

BRUCE LEHMAN

Attesting Officer

Commissioner of Patents and Trademarks